(12) United States Patent
Westman

(10) Patent No.: US 11,001,587 B2
(45) Date of Patent: May 11, 2021

(54) SUBSTITUTED INDAZOLES AS PHOSPHATIDYLINOSITOL KINASE INHIBITORS

(71) Applicant: CUROVIR AB, Kalmar (SE)

(72) Inventor: Jacob Westman, Järlåsa (SE)

(73) Assignee: CUROVIR AB, Kalmar (SE)

( * ) Notice: Subject to any disclaimer, the term of this patent is extended or adjusted under 35 U.S.C. 154(b) by 0 days.

(21) Appl. No.: 16/495,903

(22) PCT Filed: Apr. 4, 2018

(86) PCT No.: PCT/EP2018/058522
§ 371 (c)(1),
(2) Date: Sep. 20, 2019

(87) PCT Pub. No.: WO2018/185120
PCT Pub. Date: Oct. 11, 2018

(65) Prior Publication Data
US 2020/0031833 A1    Jan. 30, 2020

(30) Foreign Application Priority Data

Apr. 5, 2017   (EP) .................................... 17165082

(51) Int. Cl.
| | | |
|---|---|---|
| *A61K 31/416* | (2006.01) | |
| *C07D 231/56* | (2006.01) | |
| *C07D 487/04* | (2006.01) | |
| *A61P 31/12* | (2006.01) | |

(52) U.S. Cl.
CPC ............ *C07D 487/04* (2013.01); *A61P 31/12* (2018.01)

(58) Field of Classification Search
CPC ............................ A61K 31/416; C07D 231/56
USPC ........................................ 514/403; 548/361.1
See application file for complete search history.

(56) References Cited

U.S. PATENT DOCUMENTS 6,313,124 B1   11/2001   He et al.

FOREIGN PATENT DOCUMENTS

| WO | 2007038314 A2 | 4/2007 |
|---|---|---|
| WO | WO2010086040 A1 | 8/2010 |
| WO | WO2013128029 A1 | 9/2013 |
| WO | WO2015110491 A2 | 7/2015 |
| WO | WO2016206999 A1 | 12/2016 |
| WO | WO 18/185120 | * 10/2018 |

OTHER PUBLICATIONS

Jordan, V. C. Nature Reviews: Drug Discovery, 2, 2003, 205.*
Dörwald, F. Zaragoza. Side Reactions in Organic Synthesis: A Guide to Successful Synthesis Design, Weinheim: Wiley-VCH Verlag GmbH & Co. KGaA, 2005, Preface.*
Hackam, et al. JAMA, 296(14), 2006, 1731-1732.*
Barlow, et al, "Autophagy in Diabetes:?-Cell Dysfunction, Insulin Resistance, and Complications," DNA and Cell. Biol, 2015, 34(4), 252-260).
Bianco et al., "Metabolism of Phosphatidylinositol 4-Kinase IIIα-Dependent PI4P Is Subverted by HCV and Is Targeted by a 4-Anilino Quinazoline with Antiviral Activity," PLoS Pathogens, 2012, 8(3), 1-17).
Catalano et al., "Phenoxide leaving group SNAr strategy for the facile preparation of 7-amino-3-aryl pyrazolo[1,5-a]pyrimidines from a 3-bromo-7-phenoxypyrazolo[1,5-a]pyrimidine intermediate," Tetrahedron Lett. 2015, 56, 6077-6079.
Chen et al. , "Optimization of 3-phenylpyrazolo[1,5-a]pyrimidines as potent corticotropin-releasing factor-1 antagonists with adequate lipophilicity and water solubility," Bioorg. Med. Chem. Lett. 2004, 14, 3669-3673.
Décor et al., "Design, synthesis and biological evaluation of novel aminothiazoles as antiviral compounds acting against human rhinovirus," Bioorg. Med. Chem. Letters 23 2013, 3841-3847.
Gilligan et al., "8-(4-Methoxyphenyl) pyrazolo[1,5-a]-1,3,5-triazines: Selective and Centrally Active Corticotropin-Releasing Factor Receptor-1 (CRF1) Antagonists," J. Med. Chem. 2009, 52, 3073-3083.
Griffith et al., "Discovery and evaluation of pyrazolo[1,5-a]pyrimidines as neuropeptide Y1 receptor antagonists," Bioorg. Med. Chem. Lett. 2011, 21, 2641-2645.
Gudmundsson et al., "Pyrazolopyrimidines and pyrazolotriazines with potent activity against herpesviruses," Bioorg. Med. Chem. Lett. 2009, 19, 5689-5692.
Hwang et al., "Discovery and characterization of a novel 7-aminopyrazolo[l,5-a]pyrimidine analog as a potent hepatitis C virus inhibitor," Bioorg. Med. Chem. Lett. 2012, 22, 7297-7301.
Kusakabe, "Discovery of Imidazo[ 1,2-b] pyridazine Derivatives: Selective and Orally Available Mps1 (TTK) Kinase Inhibitors Exhibiting Remarkable Antiproliferative Activity," J. Med. Chem. 2015, 58, 1760-1775.
Labroli et al., "Discovery of pyrazolo[1,5-a]pyrimidine-based CHK1 inhibitors:A template-based approach—Part 2," Bioorg. Med. Chem. Lett. 2011, 21, 471-474.
Lai et al., "The Autophagic Machinery in Enterovirus Infection," Viruses, 2016, 8(32), 1-13.

(Continued)

*Primary Examiner* — Douglas M Willis
(74) *Attorney, Agent, or Firm* — Renner Otto Boisselle & Sklar, LLP

(57) ABSTRACT

A compound of formula (I)

or a pharmaceutically acceptable salt thereof, useful in therapy, in particular in the treatment of a viral infection or a disease linked to impaired or abnormal autophagy.

19 Claims, 5 Drawing Sheets

(56) References Cited

OTHER PUBLICATIONS

Lamarche et al., "Anti-Hepatitis C Virus Activity and Toxicity of Type III Phosphatidylinositol-4-Kinase Beta Inhibitors," Antimicrobial Agents and Chemotherapy 2012, 56(10), 5149-5156.
Levine et al., "Autophagy in the Pathogenesis of Disease," Cell, 2008, 132(1), 27-42.
Majo et al., "Facile Palladium-Catalyzed Synthesis of 3-Arylpyrazolo-[1,5-a] pyrimidines," Adv. Synth. Catal. 2003, 345, 620-624.
McLeod et al., "Identification of a Series of Compounds with Potent Antiviral Activity for the Treatment of Enterovirus Infections," ACS Med. Chem. Lett. 2013, 4(7), 585-589.
Mejdrova et al., "Highly Selective Phosphatidylinositol 4-Kinase IIIβ Inhibitors and Structural Insight into Their Mode of Action," (J. Med. Chem., 2015, 58 (9), 3767-3793.
Mejdrova et al., "Rational Design of Novel Highly Potent and Selective Phosphatidylinositol 4-Kinase IIIβ (PI4KB) Inhibitors as Broad-Spectrum Antiviral Agents and Tools for Chemical Biology," J. Med. Chem., 2017, 60 (1), 100-118.
Polajnar et al., "Impaired autophagy: a link between neurodegenerative and neuropsychiatric diseases," J Cell. Mol. Med. 2014, 9(18). 1705-1711.
Sala et al , "Purine analogs as phosphatidylinositol 4-kinase IIIβ inhibitors," Bioorg. Med. Chem. Lett. 2016, 26(11), 2706-2712.
Sridhar et al., "The lipid kinase PI4KIIIβ preserves lysosomal identity," EMBO J. 2013,32, 324-339.
Tellew et al., "Discovery of NBI-77860/GSK561679, a potent corticotropin-releasing factor ( CRF1 ) receptor antagonist with improved pharmacokinetic properties," Bioorg. Med. Chem. Lett. 2010, 20, 7259-7264.
Van Der Schaar et al., "A Novel, Broad-Spectrum Inhibitor of Enterovirus Replication That Targets Host Cell Factor Phosphatidylinositol 4-Kinase IIIβ," Antimicrobial Agents Chemother. 2013, 57(10), 4971-4981.
Wagner et al., "A Selective Cannabinoid-1 Receptor Antagonist, PF-95453, Reduces Body Weight and Body Fat to a Greater Extent than Pair-Fed Controls in Obese Monkeys," Pharm. Exp. Ther. (2010), 335(1), 103-113.
Yang et al., "Phosphatidylinositol 4-Kinase IIIβ Is Required for Severe Acute Respiratory Syndrome Coronavirus Spike-mediated Cell Entry," J. Biol. Chem. 2012, 287(11), 8547-8467.
International Search Report and Written Opinion for corresponding International Application No. PCT/EP2018/058522 dated Jun. 19, 2018.

* cited by examiner

SUBSTITUTED INDAZOLES AS PHOSPHATIDYLINOSITOL KINASE INHIBITORS

This application is a national phase of International Application No. PCT/EP2018/058522 filed Apr. 4, 2018 and published in the English language, which claims priority to European Application No. 17165082.3 filed Apr. 5, 2017, both of which are hereby incorporated herein by reference.

FIELD OF THE INVENTION

The present invention relates generally to novel compounds having usefulness in therapy, in particular in the treatment of viral conditions, more particularly viral conditions caused by picornaviruses, e.g. enteroviruses. The present invention also relates to novel compounds having usefulness for the treatment of diseases such as meningitis, hand-foot and mouth disease, herpangina, respiratory disease, encephalitis and myocarditis, but also including diabetes, cancer, neurodegenerative diseases such as Alzheimer's disease and amyotrophic lateral sclerosis.

BACKGROUND OF THE INVENTION

Pyrazolo[1,5-a]pyrimidine derivatives have been described as analgesics, benzodiazepine receptor antagonists, angiotensin II receptor antagonists, angiogenesis inhibitors, anti-inflammatory agents, neuropeptide Y receptor antagonists, COX2-inhibitor and corticotrophin-releasing hormone receptor type 1 antagonists and as CHK1 inhibitors (e.g. Mayo et al (Adv. Synth. Catal. 2003, 345, 620-624; Tellew et al (Bioorg. Med. Chem. Lett. 2010, 20, 7259-7264); Chen et al (Bioorg. Med. Chem. Lett. 2004, 14, 3669-3673); Labroli et al (Bioorg. Med. Chem. Lett. 2011, 21, 471-474); Griffith et al (Bioorg. Med. Chem. Lett. 2011, 21, 2641-2645); Gilligan et al, (J. Med. Chem. 2009, 52, 3073-3083); He et al. (U.S. Pat. No. 6,313,124 B1); and Wren et al. (WO 2010/086040), Catalano et al (Tetrahedron Lett. 2015, 56, 6077-6079). The pyrazolo[1,5-a]pyrimidine scaffold has also been described in phosphatidylinositol 4-kinase (PI4K) inhibitors. Bianco et al (PLoS Pathogens, 2012, 8(3), 1-17) and LaMarche et al (Antimicr. Agents and Chemother. 2012, 56(10), 5149-5156) have shown that PI4K is important for hepatitis C virus (HCV) replication and Yang et al (J. Biol. Chem. 2012, 287(11), 8547-8467) have shown the same for coronavirus. Gudmundsson et al (Bioorg. Med. Chem. Lett. 2009, 19, 5689-5692) have disclosed some 3-arylpyrazolo[1,5-a]pyrimidines with potent activity against herpes virus. Hwang et al (Bioorg. Med. Chem. Lett. 2012, 22, 7297-7301) have described 3-arylpyrazolo[1,5-a]pyrimidines as PI4K inhibitors that have anti-HCV effects. In WO 2015/110491 some further pyrazolo[1,5-a]pyrimidine derivatives are described as PI4KIIIβ inhibitors having an antiviral activity. Pyrazolo[1,5-a][1,3,5]triazine derivatives have been described as corticotropin-releasing factor receptor-1 (CRF1) antagonists which may be potential anxiolytic and antidepressant drugs (cf. for example, Gilligan et al (J. Med. Chem. 2009, 52, 3073-3083). Pexacerfont is a clinically tested pyrazolo[1,5-a] triazin-4-amine drug developed by Bristol-Myers Squibb, acting as a CRF-1 antagonist. The pyrazolo[1,5-a][1,3,5] triazine scaffold has also been described as present in cyclin-dependent kinase inhibitors (WO2013128029), casein kinase inhibitors and DYRK1A kinase inhibitors (WO2010103486) useful for treatment of various diseases. The scaffold has further been described as present in cannabinoid 1 receptor antagonists (J. Pharm. Exp. Ther. (2010), 335(1), 103-113). Pyrazolo[1,5-a] triazin-4-amines have been described as PI4K inhibitors with antiviral potency in Mejdrova et al (J. Med. Chem., 2015, 58 (9), 3767-3793), and in Mejdrova et al (J. Med. Chem., 2017, 60 (1), 100-118). In WO2016206999 some further pyrazolo[1, 5-a]triazine derivatives are described as PI4KIIIβ inhibitors having an antiviral activity.

Imidazo[1,2-b]pyridazine derivatives have been described as Mps1 kinase inhibitors (Kusakabe, J. Med. Chem. 2015, 58, 1760-1775). Similar scaffolds have been described as present in phosphatidylinositol 4-kinase (PI4K) inhibitors (McLeod et al (ACS Med. Chem. Lett. 2013, 4(7), 585-589) and van der Schaar et al (Antimicrobial Agents Chemother. 2013, 57(10), 4971-4981), and inhibitors of PI4K have been shown to be potent antivirals (Bianco et al, PLoS Pathogens, 2012, 8(3), 1-17; LaMarche et al, Antimicr. Agents and Chemother. 2012, 56(10), 5149-5156; Décor et al, Bioorg. Med. Chem. Lett. 2013, 23, 3841-7).

Décor et al (Bioorg. Med. Chem. Lett. 2013, 23, 3841-7) have also shown that PI4K is important for enterovirus replication. However, they have also shown that PI4K inhibitors (non 3-arylpyrazolo[1,5-a]pyrimidines) and the 3-arylpyrazolo[1,5-a]pyrimidine dimethoxyphenyl)-2,5-dimethyl-N-(2-morpholinoethyl)pyrazolo[1,5-a]pyrimidin-7-amine (called T-00127-HEV1) when tested in-vivo induced mortality in mice, which raised doubts on the safety of inhibiting PI4K. Sala et al (Bioorg. Med. Chem. Lett. 2016, 26(11), 2706-12) have published several analogs based on the PI4KIIIβ inhibitor T-00127-HEV1. The authors made a number of analogs with modifications in the central rings of the compounds.

Autophagy is a process of homeostatic degradation in cells, used to create nutrients in times of stress and as a mechanism to recycle damaged organelles or microbes in the cytostol (Karanasios et al, 2016, Autophagy at the cell, tissue and organismal level (Springer)). Many pathogens interact with the host autophagic pathways and could impair the normal autophagy. Lai et al (Viruses, 2016, 8(32), 1-13) describe that viruses subvert the autophagy machinery to benefit the virus replication and exit from the host and that inhibition of PI4K111β will have an effect on the autophagy processes and thus inhibit the virus replication. Sridhar et al (EMBO J. 2013, 32, 324-339) describe PI4K111β to be a key factor in autophagy and it is believed that many diseases are caused by or linked to impaired or abnormal autophagy, for example neurodegenerative and neuropsychiatric diseases, cancer, cardiac diseases, inflammatory diseases and diabetes (Polajnar et al J. Cell. Mol. Med. 2014, 9(18). 1705-1711; Levine et al, Cell, 2008, 132(1), 27-42; Barlow, et al, DNA Cell. Biol, 2015, 34(4), 252-260). Without being bound to any theory it is believed that compounds of the present invention also could be used for treatment of diseases caused by or linked to impaired or abnormal autophagy.

There remains a need for novel, therapeutically active compounds, e.g. antiviral agents.

SUMMARY OF THE INVENTION

A first aspect is a compound of formula (I)

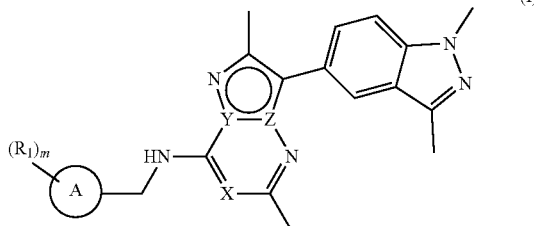

or a pharmaceutically acceptable salt thereof, wherein
X is CH or N;
Y is N and Z is C; or Y is C and Z is N;
the 5-membered ring containing N, Y and Z is a heteroaromatic ring;
ring A is phenyl or 5- or 6-membered heteroaryl having one or more, e.g. one or two, heteroatoms independently selected from N, O and S;
m is 0, 1 or 2;
each $R_1$ is independently selected from halogen, C1-C6 alkyl, $R_2O$, $R_3S(O)_2$, $R_4S(O)_2N(R_5)$, $R_6R_7NC(O)$, $R_8C(O)N(R_9)$, $R_{10}C(O)$, $R_{11}R_{12}N$, and $R_{13}R_{14}NS(O)_2$, and when m is 2, two $R_1$ attached to adjacent atoms of ring A, together with the atoms to which they are attached, may form a 5- or 6-membered heterocyclic or carbocyclic ring;
each one of $R_2$, $R_3$, $R_4$, $R_5$, $R_6$, $R_7$, $R_8$, $R_9$, $R_{10}$, $R_{11}$, $R_{12}$, and $R_{13}$ is independently selected from H and C1-C6 alkyl;
$R_{14}$ is selected from H, C1-C6 alkyl, $R_{15}C(O)$, and $R_{16}OC(O)$;
$R_{15}$ and $R_{16}$ are independently selected from H and C1-C6 alkyl; and
any alkyl is optionally substituted by one or more halogen.

A further aspect is a compound of formula (I), or a pharmaceutically acceptable salt thereof, for use as an inhibitor of picornavirus replication.

A further aspect is a compound of formula (I), or a pharmaceutically acceptable salt thereof, for use as an inhibitor of picornaviral cytopathogenic effects.

A further aspect is a compound of formula (I), or a pharmaceutically acceptable salt thereof, for use as an inhibitor of phosphatidylinositol 4-kinase IIIβ.

A further aspect is a compound of formula (I), or a pharmaceutically acceptable salt thereof, for use to modulate autophagy.

A further aspect is a compound of formula (I), or a pharmaceutically acceptable salt thereof, for use in therapy.

A still further aspect is a pharmaceutical composition comprising a compound of formula (I), or a pharmaceutically acceptable salt thereof, and optionally a pharmaceutically acceptable excipient.

A further aspect is a compound of formula (I), or a pharmaceutically acceptable salt thereof, for use in the treatment of a viral infection.

A further aspect is a compound of formula (I), or a pharmaceutically acceptable salt thereof, capable of improving impaired or modulating abnormal autophagy in a cell, for use in the treatment of a disease as mentioned herein.

A further aspect is a compound of formula (I), or a pharmaceutically acceptable salt thereof, for use in the treatment of a disease linked to impaired or abnormal autophagy.

A further aspect is a compound of formula (I), or a pharmaceutically acceptable salt thereof, for use in the treatment of a disease linked to impaired autophagy.

A further aspect is a compound of formula (I), or a pharmaceutically acceptable salt thereof, for use in the treatment of a disease linked to abnormal autophagy.

By "abnormal autophagy" is meant e.g. autophagy that favours viral replication and release.

By "impaired autophagy" is meant a subnormally functioning autophagy in a cell.

A disease linked to impaired or abnormal autophagy that may be treated according to the invention e.g. may be selected from neurodegenerative and neuropsychiatric diseases, cancer, cardiac diseases, inflammatory diseases and diabetes, such as diseases mentioned herein.

A further aspect is a compound of formula (I), or a pharmaceutically acceptable salt thereof, for use in the treatment of a non-enveloped single-stranded (+) RNA viral infection.

Still a further aspect is a compound of formula (I), or a pharmaceutically acceptable salt thereof, for use in the treatment of pancreatitis, poliomyelitis, encephalitis, meningitis, sepsis, cancer, such as breast, prostate, ovarian and colorectal cancer, paralysis, cardiac diseases, such as myocarditis, diabetes, common cold, hand-foot-and-mouth disease, herpangina, pleurodynia, diarrhea, mucocutaneous lesions, respiratory illness, conjunctivitis, myositis, chronic fatigue syndrome, neuropsychiatric diseases, and neurodegenerative diseases such as multiple sclerosis, Parkinson's disease, amyotrophic lateral sclerosis, Alzheimer's disease, and Huntington's disease, or inflammatory conditions.

A further aspect is the use of a compound of formula (I) or a pharmaceutically acceptable salt thereof in the manufacture of a medicament for the treatment of a disorder or disease as mentioned herein.

A further aspect is a method for the treatment of a disorder or disease as mentioned herein by administration of a therapeutically effective amount of a compound of formula (I) or a pharmaceutically acceptable salt thereof to a mammal in need thereof.

DETAILED DESCRIPTION OF THE INVENTION

Figure 1:
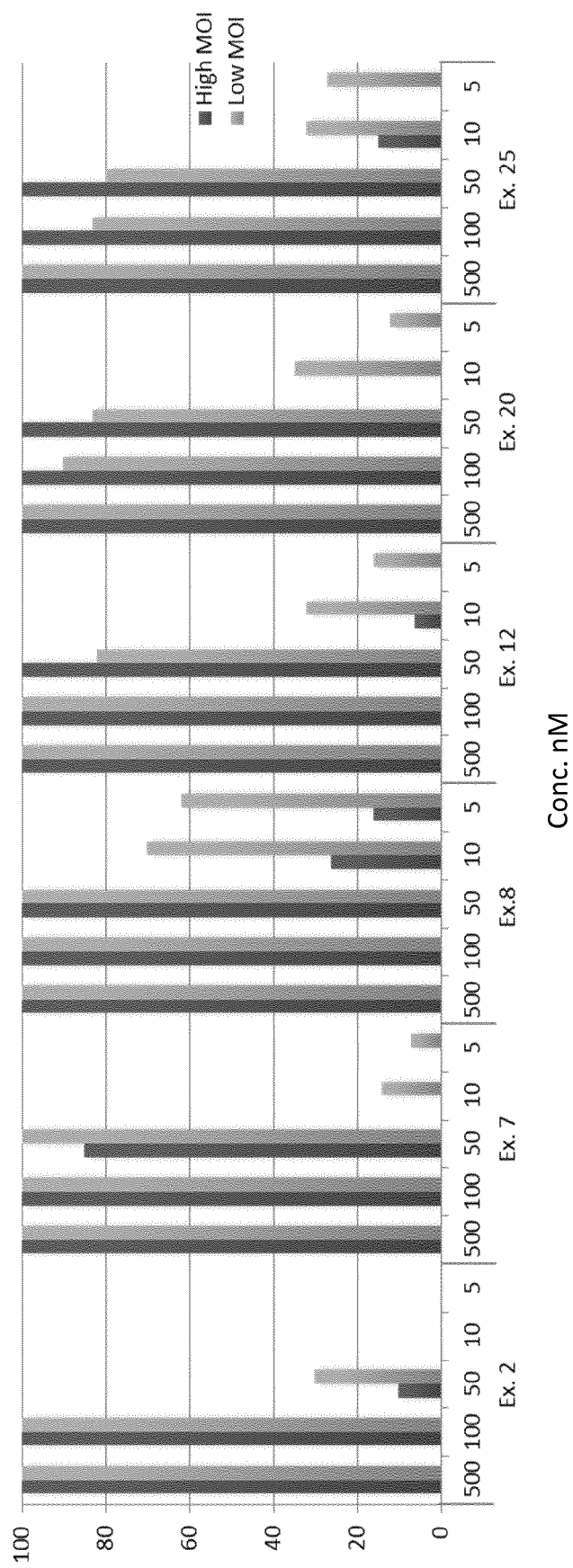
FIG. 1 is a bar chart showing the dose response of inhibition of Coxsackie B3 Nancy strain induced cytopathogenic effect by addition of 6 different compounds of the present invention, at two different concentration of the virus to the cells at infection.

"Pharmaceutically acceptable" means being useful in preparing a pharmaceutical composition that is generally safe, non-toxic and neither biologically nor otherwise undesirable and includes being useful for veterinary use as well as human pharmaceutical use.

"Treatment" as used herein includes prophylaxis of the named disorder or condition, or amelioration or elimination (i.e. cure) of the disorder once it has been established.

An "effective amount" refers to an amount of a compound that confers a therapeutic effect on the treated subject. The therapeutic effect may be objective (i.e., measurable by some test or marker, e.g. no measurable virus titre in a biological sample from the treated subject) or subjective (i.e., subject gives an indication of or feels an effect).

Unless otherwise stated or indicated, the term "C1-C6 alkyl" denotes a straight or branched alkyl group having from 1 to 6 carbon atoms, e.g. methyl, ethyl, n-propyl, iso-propyl, n-butyl, iso-butyl, sec-butyl, t-butyl and straight- and branched-chain pentyl and hexyl.

Unless otherwise stated or indicated, the term "halogen" (or "halo") refers to fluorine (F), chlorine (Cl), or bromine (Br).

A moiety of the type RO is a moiety of formula

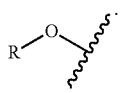

A moiety of the type RR'NC(O) is a moiety of formula

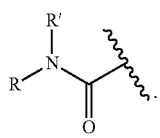

A moiety of the type RC(O)N(R') is a moiety of formula

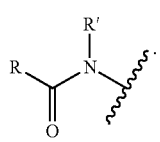

A moiety of the type RS(O)$_2$ is a moiety of formula

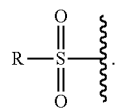

A moiety of the type RS(O)$_2$N(R') is a moiety of formula

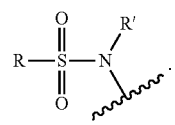

A moiety of the type RR'NS(O)$_2$ is a moiety of formula

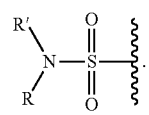

A moiety of the type RR'N is a moiety of formula

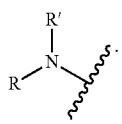

A moiety of the type RC(O) is a moiety of formula

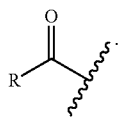

A moiety of the type ROC(O) is a moiety of formula

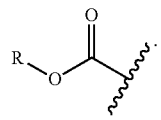

The term "heterocyclyl" (or "heterocyclic ring") refers to a saturated or unsaturated, aromatic or non-aromatic cyclic moiety containing not only carbon atoms, but also at least one other atom in the ring, e.g. selected from nitrogen (N), sulphur (S) and oxygen (O). When aromatic, the heterocyclyl also may be referred to as "heteroaryl", which refers to an aromatic ring containing at least one ring heteroatom, such as furyl, isoxazolyl, isothiazolyl, imidazolyl, pyridyl, pyrrolyl, pyrazolyl, pyrimidinyl, pyridazinyl, pyrazinyl, oxadiazolyl, oxazolyl, thienyl, thiadiazolyl, thiazolyl, triazolyl, and tetrazolyl.

The term "aromatic", as used herein, refers to an unsaturated cyclic moiety that has an aromatic character, while the term "non-aromatic", as used herein, refers to a cyclic moiety, that may be saturated or unsaturated, e.g. polyunsaturated, but that does not have an aromatic character.

The term "benzyl" refers to a moiety of formula C₆H₅CH₂—, i.e.;

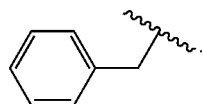

The term "pyridyl" (or pyridinyl) refers to a moiety of formula

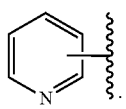

The term "3-pyridyl" (or "pyridin-3-yl") refers to a moiety of formula

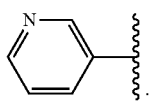

A 3-pyridyl substituted with a moiety $R_1$ in 6-position (e.g. 6-methyl-3-pyridyl) is a compound of formula

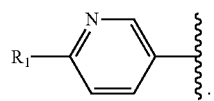

The term "4-pyridyl" (or pyridin-4-yl) refers to a moiety of formula

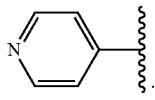

The term "thienyl" refers to a moiety of formula

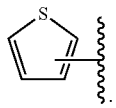

The term "2-thienyl" refers to a moiety of formula

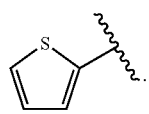 [SMILES: *c1ccco1]

The term "furyl" refers to a moiety of formula

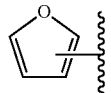

The term "2-furyl" refers to a moiety of formula

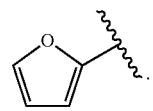

A "non-enveloped single-stranded (+) RNA viral infection" refers to an infection with a non-enveloped single-stranded (+) RNA virus. A "non-enveloped virus" is a virus lacking viral envelope. A "single-stranded (+) RNA virus" is a virus having genetic material which is single-stranded RNA and which RNA can be immediately translated to viral protein by the cell infected by the virus.

The term "mammal" refers to a human or any mammalian animal, e.g. a primate, a farm animal, a pet animal, or a laboratory animal. Examples of such animals are monkeys, cows, sheep, goats, horses, pigs, dogs, cats, rabbits, mice, rats etc. Preferably, the mammal is a human. In some embodiments, however, the mammal is an animal, e.g. a farm animal, such as a cow, sheep, goat, horse, or pigs. In some other embodiments, the animal is a pet, e.g. a dog, a cat or a rabbit.

The term "excipient" refers to a pharmaceutically acceptable chemical, such as known to those of ordinary skill in the art of pharmacy to aid the administration of a medicinal agent. It is a compound that is useful in preparing a pharmaceutical composition, generally safe, non-toxic and neither biologically nor otherwise undesirable, and includes excipients that are acceptable for veterinary use as well as human pharmaceutical use. Exemplary excipients include binders, surfactants, diluents, disintegrants, antiadherents, and lubricants.

In a compound of formula (I) as defined herein, X is N or CH; and Y is N and Z is C, or Y is C and Z is N. In some embodiments, X is CH, Y is N, and Z is C; or X is CH, Y is C, and Z is N; or X is N, Y is N, and Z is C. In some embodiments, X is CH, Y is N, and Z is C; or X is CH, Y is C, and Z is N. In some embodiments, X is CH, Y is C, and Z is N; or X is N, Y is N, and Z is C. In some embodiments, X is CH, Y is N, and Z is C; or X is N, Y is N, and Z is C.

In some embodiments, X is CH, i.e. the compound of formula (I) is a compound of formula (Ia)

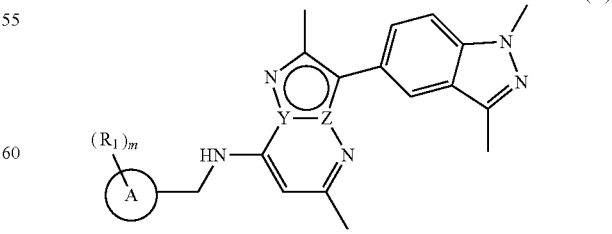

(Ia)

wherein m, $R_1$, ring A, Y and Z are as defined herein.

In some embodiments, X is N, i.e. the compound of formula (I) is a compound of formula (Ib)

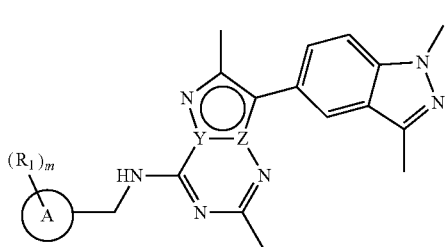

(Ib)

wherein m, R₁, ring A, Y and Z are as defined herein.

In some embodiments, Y is C and Z is N, i.e. the compound of formula (I) is a compound of formula (Ic)

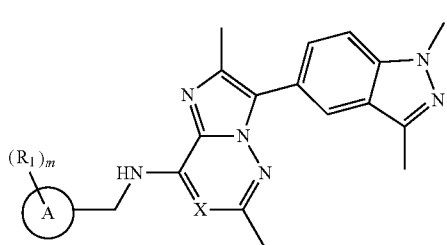

(Ic)

wherein m, R₁, ring A, and X are as defined herein.

In some embodiments, Y is N and Z is C, i.e. the compound of formula (I) is a compound of formula (Id)

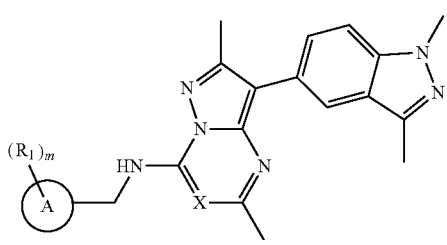

(Id)

wherein m, R₁, ring A, and X are as defined herein.

In some embodiments of a compound of formula (Ia), Y is C and Z is N, i.e. the compound may be represented by formula (Ie)

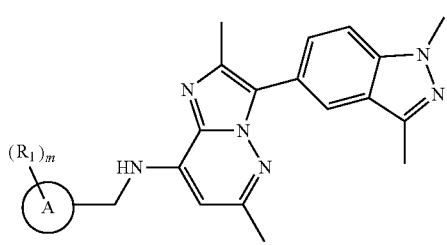

(Ie)

wherein m, R₁, and ring A are as defined herein.

In some other embodiments of a compound of formula (Ia), Y is N and Z is C, i.e. the compound may be represented by formula (If)

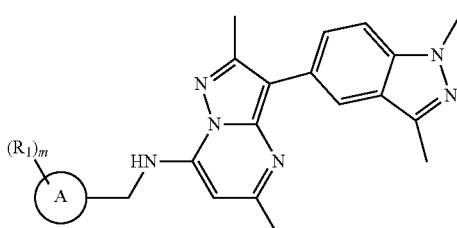

(If)

wherein m, R₁, and ring A are as defined herein.

In some embodiments of a compound of formula (Ib), Y is N and Z is C, i.e. the compound may be represented by formula (Ig)

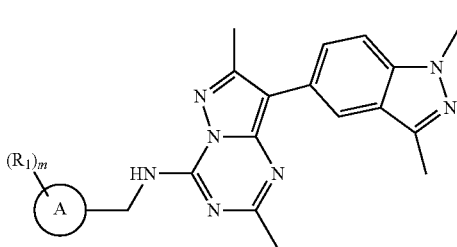

(Ig)

wherein m, R₁, and ring A are as defined herein.

In some embodiments of a compound of formula (Ib), Y is C and Z is N, i.e. the compound may be represented by formula (Ih)

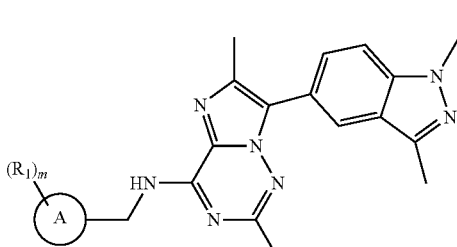

(Ih)

wherein m, R₁, and ring A are as defined herein.

In some of embodiments of a compound of formula (I), X is N only when Y is N and Z is C.

In a compound of formula (I), ring A is phenyl or 5- or 6-membered heteroaryl having one or more heteroatoms selected from O, S, and N. In some embodiments, ring A is 5- or 6-membered heteroaryl. In some other embodiments, ring A is phenyl or 6-membered heteroaryl. In still other embodiments, ring A is phenyl. In still other embodiments, ring A is phenyl or 5-membered heteroaryl. In some embodiments, ring A is 5-membered heteroaryl. In some other embodiments, ring A is 6-membered heteroaryl.

When ring A is 5- or 6-membered heteroaryl, said heteroaryl contains one or more heteroatoms selected from N, O and S. For example, said heteroaryl may contain 1, 2, 3, or 4 heteroatoms. In some embodiments, said heteroaryl contains 1, 2 or 3 heteroatoms. In some other embodiments, said heteroaryl contains or 1 or 2 heteroatoms selected from N, O and S. In still other embodiments, said heteroaryl contains 1 heteroatom selected from N, O and S.

When ring A is heteroaryl, each heteroatom is independently selected from N, O and S. In some embodiments, each heteroatom is independently selected from N and O. In still other embodiments each heteroatom is independently selected from N and S. In some particular embodiments, at least one heteroatom is N, e.g. each heteroatom is N. In some embodiments, the heteroaryl contains one heteroatom, which is N. In some other embodiments, the heteroraryl contains one heteroatom, which is O. In some other embodiments, the heteroaryl contains one heteroatom, which is S.

In some embodiments, when ring A is 5-membered heteroaryl, said heteroaryl contains one heteroatom selected from O and S, and optionally one or more nitrogen atoms, e.g. 1-3 N, or 1 or 2 N, e.g. 1 N. In some embodiments, said heteroaryl is thienyl or furyl, e.g. 2-thienyl or 2-furyl. In some embodiments, when ring A is 5-membered heteroaryl, said heteroaryl more particularly is thienyl, e.g. 2-thienyl.

In some embodiments, when ring A is 6-membered heteroaryl, each heteroatom of said heteroaryl is N. For example, in some embodiments, when ring A is 6-membered heteroaryl, said heteroaryl is pyridyl, e.g. 3-pyridyl or 4-pyridyl.

In some embodiments, when ring A is 5- or 6-membered heteroaryl, said heteroaryl is selected from thienyl, furyl, pyrrolyl, imidazolyl, pyrazolyl, thizaolyl, isothiazolyl, oxazolyl, isoxazolyl, triazolyl, tetrazolyl, oxadiazolyl, thiadiazolyl, pyridyl, pyrazinyl, pyrimidinyl, and pyridazinyl.

The compound of formula (I) comprises a moiety of formula (II)

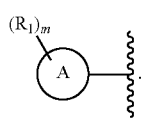

(II)

In some embodiments, when ring A is phenyl or 6-membered heteroaryl, the moiety of formula (II) more particularly is a moiety of formula (IIa)

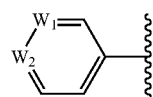

(IIa)

wherein $W_1$ and $W_2$ are independently selected from N, CH and $CR_1$. In such embodiments, the compound of formula (I) may be represented by formula (Ij)

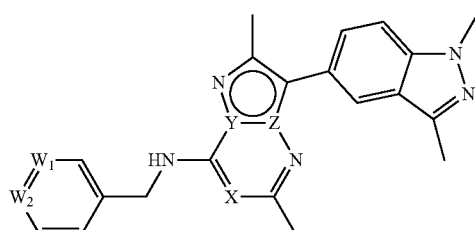

(Ij)

wherein $W_1$, $W_2$, X, Y and Z are as defined herein.

In some embodiments, one of $W_1$ and $W_2$ is different from N. In some embodiments, at least one of $W_1$ and $W_2$ is N. In some embodiments, at least one of $W_1$ and $W_2$ is different from CH. In some embodiments, at least one of $W_1$ and $W_2$ is different from $CR_1$. In some embodiments, $W_1$ and $W_2$ are different from each other, i.e. $W_1$ and $W_2$ are not both N, not both CH and not both $CR_1$.

In some particular embodiments of a compound of formula (Ij), $W_1$ is N, CH or $CR_1$, and $W_2$ is N or $CR_1$. In some other particular embodiments, $W_1$ is CH or $CR_1$, and $W_2$ is N or $CR_1$. In some other particular embodiments, $W_1$ is N or CH, and $W_2$ is N, CH or $CR_1$. In some of these embodiments, at least one of $W_1$ and $W_2$ is different from CH. In still other embodiments of a compound of formula (Ij), either $W_1$ or $W_2$ is N, and the other one is selected from CH and $CR_1$. In some of these embodiments, $W_1$ is N, and $W_2$ is $CR_1$; or $W_1$ is CH and $W_2$ is N.

In some further embodiments, $W_1$ is CH, i.e. the compound of formula (Ij) may be represented by formula (Ik)

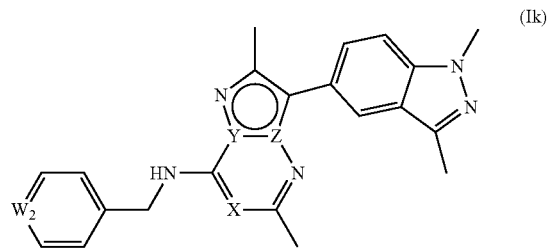

(Ik)

wherein $W_2$, X, Y and Z are as defined herein.

In some embodiments of a compound of formula (Ik), $W_2$ is N or $CR_1$, e.g. $W_2$ is N. In some other embodiments of a compound of formula (Ik), $W_2$ is CH or $CR_1$, e.g. $W_2$ is $CR_1$.

In some other particular embodiments of a compound of formula (Ij), $W_2$ is $CR_1$, i.e. the compound of formula (Ij) may be represented by formula (Im)

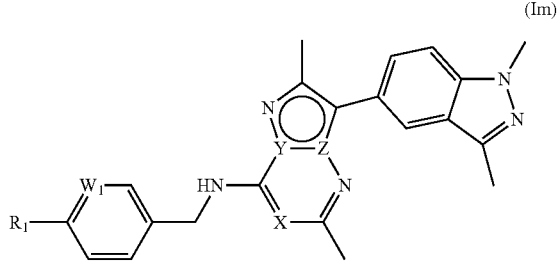

(Im)

wherein $R_1$, $W_1$, X, Y and Z are as defined herein.

In some embodiments of a compound of formula (Im), $W_1$ is N or CH, e.g. $W_1$ is N.

In some further embodiments, the moiety of formula (II)

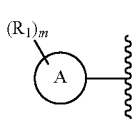

(II)

is selected from a moiety comprising 5-membered heteroaryl, e.g. unsubstituted (m is 0) 5-membered heteroaryl, and a ring of formula (IIa) as defined herein; e.g. from unsubstituted 2-thienyl and a ring of formula (IIa) wherein $W_1$ is CH and $W_2$ is $CR_1$, or $W_1$ is CH and $W_2$ is N, or $W_1$ is N and $W_2$ is $CR_1$. In some further embodiments, the moiety of formula (II) is selected from unsubstituted 2-thienyl and a ring of formula (IIa) wherein $W_1$ is CH and $W_2$ is N, or $W_1$ is N and $W_2$ is $CR_1$.

In a compound of formula (I), m is an integer that denotes the number of substituents on ring A. The integer m is 0, 1 or 2, i.e. ring A may be unsubstituted (m is 0) or substituted by 1 or 2 moieties $R_1$ (m is 1 or 2). In some embodiments, m is 0 or 1. In some other embodiments, m is 0. In still other embodiments, m is 1 or 2, in particular 1.

In some embodiments, when ring A is phenyl, m is different from 0. Thus, in some embodiments, when ring A is phenyl, m is 1 or 2, and when ring A is 5- or 6-membered heteroaryl, m is 0, 1 or 2. In some other embodiments, when ring A is phenyl, m is 1, and when ring A is 5- or 6-membered heteroaryl, m is 0 or 1. In still further embodiments, when ring A is phenyl, m is 1, and when ring A is 5- or 6-membered heteroaryl, m is 0. In some further embodiments, when ring A is phenyl, m is 1, when ring A is 5-membered heteroaryl, m is 0, and when ring A is 6-membered heteroaryl, m is 0 or 1.

In some embodiments, ring A is phenyl and m is different from 0. In some embodiments, ring A is phenyl and m is 1 or 2, or ring A is 5- or 6-membered heteroaryl and m is 0, 1 or 2. In some other embodiments, ring A is phenyl and m is 1, or ring A is 5- or 6-membered heteroaryl, and m is 0 or 1. In still further embodiments, ring A is phenyl, and m is 1, or ring A is 5- or 6-membered heteroaryl, and m is 0. In some further embodiments, ring A is phenyl, and m is 1, or ring A is 5-membered heteroaryl, and m is 0, or ring A is 6-membered heteroaryl, and m is 0 or 1.

In some embodiments, ring A is phenyl, and m is 0, 1 or 2, in particular 1 or 2. In some embodiments, ring A is phenyl, and m is 1.

In some embodiments, ring A is 5- or 6-membered heteroaryl, and m is 0 or 1. In some embodiments, ring A is 5- or 6-membered heteroaryl, and m is 0. In some embodiments, ring A is 5-membered heteroaryl, and m is 0. In some embodiments, ring A is 6-membered heteroaryl, and m is 0 or 1. In some embodiments, ring A is 6-membered heteroaryl, and m is 1. In some embodiments, ring A is 6-membered heteroaryl, and m is 0.

In a compound of formula (I), each moiety $R_1$ is independently selected from halogen, C1-C6 alkyl, $R_2O$, $R_3S(O)_2$, $R_4S(O)_2N(R_5)$, $R_6R_7NC(O)$, $R_8C(O)N(R_9)$, $R_{10}C(O)$, $R_{11}R_{12}N$, and $R_{13}R_{14}NS(O)_2$; and when m is 2, two $R_1$ attached to adjacent atoms of ring A, together with the atoms to which they are attached may form a 5- or 6-membered heterocyclic or carbocyclic ring. In some embodiments, each $R_1$ is independently selected from halogen, C1-C6 alkyl, $R_2O$, $R_3S(O)_2$, $R_4S(O)_2N(R_5)$, $R_6R_7NC(O)$, $R_8C(O)N(R_9)$, $R_{10}C(O)$, $R_{11}R_{12}N$, and $R_{13}R_{14}NS(O)_2$.

In some embodiments, each $R_1$ is independently selected from halogen, C1-C6 alkyl, $R_2O$, $R_3S(O)_2$, $R_4S(O)_2N(R_5)$, $R_8C(O)N(R_9)$, $R_{10}C(O)$, $R_{11}R_{12}N$, and $R_{13}R_{14}NS(O)_2$.

In some embodiments, each $R_1$ is independently selected from halogen, C1-C6 alkyl, $R_2O$, $R_3S(O)_2$, $R_4S(O)_2N(R_5)$, $R_6R_7NC(O)$, $R_{10}C(O)$, $R_{11}R_{12}N$, and $R_{13}R_{14}NS(O)_2$.

In some embodiments, each $R_1$ is independently selected from halogen, C1-C6 alkyl, $R_2O$, $R_3S(O)_2$, $R_4S(O)_2N(R_5)$, $R_6R_7NC(O)$, $R_8C(O)N(R_9)$, $R_{11}R_{12}N$, and $R_{13}R_{14}NS(O)_2$.

In some embodiments, each $R_1$ is independently selected from halogen, C1-C6 alkyl, $R_2O$, $R_3S(O)_2$, $R_4S(O)_2N(R_5)$, $R_6R_7NC(O)$, $R_8C(O)N(R_9)$, $R_{10}C(O)$, and $R_{13}R_{14}NS(O)_2$.

In some embodiments, each $R_1$ is independently selected from halogen, C1-C6 alkyl, $R_2O$, $R_3S(O)_2$, $R_4S(O)_2N(R_5)$, and $R_{13}R_{14}NS(O)_2$. In some embodiments, each $R_1$ is independently selected from halogen, C1-C6 alkyl, and $R_2O$.

In some embodiments, each $R_1$ is independently selected from $R_2O$, $R_3S(O)_2$, $R_4S(O)_2N(R_5)$, and $R_{13}R_{14}NS(O)_2$. In some embodiments, each $R_1$ is independently selected from $R_3S(O)_2$, $R_4S(O)_2N(R_5)$, and $R_{13}R_{14}NS(O)_2$.

In some further embodiments, each $R_1$ is independently selected from C1-C6 alkyl, $R_2O$, $R_3S(O)_2$, $R_4S(O)_2N(R_5)$, $R_6R_7NC(O)$, $R_8C(O)N(R_9)$, $R_{10}C(O)$, $R_{11}R_{12}N$, and $R_{13}R_{14}NS(O)_2$; in particular from C1-C6 alkyl, $R_2O$, $R_3S(O)_2$, $R_4S(O)_2N(R_5)$, and $R_{13}R_{14}NS(O)_2$; or from C1-C6 alkyl, $R_2O$, and $R_3S(O)_2$.

In some further embodiments, each $R_1$ is independently selected from halogen, C1-C6 alkyl, $R_2O$, and $R_3S(O)_2$.

Each one of the moieties $R_2$, $R_3$, $R_4$, $R_5$, $R_6$, $R_7$, $R_8$, $R_9$, $R_{10}$, $R_{11}$, $R_{12}$, $R_{13}$, $R_{15}$ and $R_{16}$, when present, is independently selected from H and C1-C6 alkyl, e.g. from H and C1-C4 alkyl, or from H and C1-C3 alkyl, or from H, methyl and ethyl, in particular from H and methyl.

In some embodiments, each one of the moieties $R_2$, $R_3$, $R_4$, $R_8$, $R_{10}$, $R_{15}$ and $R_{16}$, when present, is independently selected from C1-C6 alkyl, e.g. from C1-C4 alkyl, or from C1-C3 alkyl, or from methyl and ethyl, e.g. methyl; and each one of the moieties $R_5$, $R_6$, $R_7$, $R_9$, $R_{11}$, Rig, and $R_{13}$, when present, is independently selected from H and C1-C6 alkyl, e.g. from H and C1-C4 alkyl, or from H and C1-C3 alkyl, or from H, methyl and ethyl, or from H and methyl, in particular H.

In some embodiments, each one of the moieties $R_2$, $R_3$, $R_4$, $R_8$, $R_{10}$, $R_{15}$ and $R_{16}$, when present, is independently selected from C1-C3 alkyl; and each one of the moieties $R_5$, $R_6$, $R_7$, $R_9$, $R_{11}$, $R_{12}$, and $R_{13}$, and when present, is independently selected from H and C1-C3 alkyl.

In some embodiments, each one of the moieties $R_2$, $R_3$, $R_4$, $R_8$, $R_{10}$, $R_{15}$ and $R_{16}$, when present, is independently selected from methyl and ethyl; and each one of the moieties $R_5$, $R_6$, $R_7$, $R_9$, $R_{11}$, $R_{12}$, and $R_{13}$, when present, is independently selected from H, methyl and ethyl.

In some particular embodiments, each one of the moieties $R_2$, $R_3$, $R_4$, $R_8$, $R_{10}$, $R_{15}$ and $R_{16}$, when present, is methyl; and each one of the moieties $R_5$, $R_6$, $R_7$, $R_9$, $R_{11}$, $R_{12}$, and $R_{13}$, and when present, is H.

The moiety $R_{14}$ is selected from H, C1-C6 alkyl, $R_{15}C(O)$, and $R_{16}OC(O)$. In some embodiments, $R_{14}$ is H or C1-C6 alkyl, e.g. H or C1-C4 alkyl; or H or C1-C3 alkyl; or H, methyl or ethyl; in particular H or methyl; e.g. $R_{14}$ is H. In some other embodiments, $R_{14}$ is selected from H, $R_{15}C(O)$, and $R_{16}OC(O)$, e.g. from H and $R_{15}C(O)$, e.g. $R_{14}$ is $R_{15}C(O)$. In still further embodiments, $R_{14}$ is selected from C1-C6 alkyl, RisC(O), and $R_{16}OC(O)$; e.g. from RisC(O) and $R_{16}OC(O)$, e.g. $R_{14}$ is $R_{16}OC(O)$. In some further embodiments, $R_{14}$ is C1-C6 alkyl, e.g. C1-C4 alkyl; or C1-C3 alkyl; e.g. methyl or ethyl; in particular methyl.

When $R_1$ is C1-C6 alkyl, said alkyl more particularly may be C1-C4 alkyl, or C1-C3 alkyl, or C1-C2 alkyl, e.g. methyl.

When $R_1$ is halogen, said halogen e.g. may be F, Cl or Br; or F or Cl; in particular Cl. In some embodiments, $R_1$ is Cl or Br.

In some particular embodiments, each $R_1$ is independently selected from F, Cl, $CH_3$, $CF_3$, $CH_3O$, $CH_3S(O)_2$, $CH_3S(O)_2NH$, and $NH_2S(O)_2$; or from Cl, $CH_3$, $CH_3O$, $CH_3S(O)_2$, $CH_3S(O)_2NH$, and $NH_2S(O)_2$; e.g. from $CH_3$, $CH_3O$, $CH_3S(O)_2$, $CH_3S(O)_2NH$, and $NH_2S(O)_2$; or from $CH_3$, $CH_3O$, and $CH_3S(O)_2$.

In a compound of formula (I), any alkyl may optionally be substituted by one or more halogen atoms. In some embodiments, when any alkyl is substituted by one or more halogen, the halogen is fluoro (F). In some embodiments, no halogen substitution is present on any alkyl.

It should be noted that any reference to a compound of formula (I) implicitly also is a reference to a compound of any of the embodiments of such a compound, as illustrated in the formulas (Ia) to (Im), unless otherwise indicated or apparent from the context. Furthermore, unless mutually exclusive, and whether illustrated herein or not, any combinations of the embodiments as illustrated by formulas (Ia) to (Im) is contemplated within the scope of formula (I). For example, in some embodiments, a compound of formula (Ia) also is a compound of formula (Ic), i.e. a compound as illustrated by formula (Ie). In some other embodiments, a compound of formula (Ia) also is a compound of formula (Id), i.e. a compound as illustrated by formula (If).

Likewise, in some embodiments, a compound of formula (Ia) also is a compound of formula (Ij). In some embodiments, a compound of formula (Ib) also is a compound of formula (Ij). In some embodiments, a compound of formula (Ic) also is a compound of formula (Ij). In some embodiments, a compound of formula (Id) also is a compound of formula (Ij).

In some embodiments of a compound of formula (I), X is CH, Y is N and Z is C, or X is CH, Y is C and Z is N; or X is N, and Y is N and Z is C; and ring A is phenyl, thienyl, or pyridyl, e.g. ring A is phenyl, 2-thienyl, 3-pyridyl, or 4-pyridyl. In some of these embodiments, when ring A is phenyl, m is 1, and when ring A is thienyl or pyridyl, m is 0 or 1; e.g., when ring A is phenyl, m is 1; when ring A is thienyl, m is 0; and when ring A is pyridyl, m is 0 or 1. In some of these embodiments, $R_1$ is halogen, C1-C6 alkyl, $R_2O$, $R_3S(O)_2$, $R_4S(O)_2N(R_5)$, or $R_{13}R_{14}NS(O)_2$; each one of $R_2$, $R_3$, $R_4$, $R_5$, $R_{13}$ and $R_{10}$ is independently selected from H and C1-C6 alkyl; e.g. from H and C1-C3 alkyl, and any alkyl is optionally substituted by one or more halogen.

In some particular embodiments of a compound of formula (I),
X is CH, Y is N, and Z is C; or X is CH, Y is C, and Z is N; or X is N, Y is N, and Z is C; ring A is phenyl or 5- or 6-membered heteroaryl having one heteroatom, which heteroatom is selected from N, O and S;
m is 0 or 1;
each $R_1$ is independently selected from halogen, C1-C6 alkyl, $R_2O$, $R_3S(O)_2$, $R_4S(O)_2N(R_5)$, $R_6R_7NC(O)$, $R_8C(O)N(R_9)$, $R_{10}C(O)$, $R_{11}R_{12}N$, and $R_{13}R_{14}NS(O)_2$;
each one of $R_2$, $R_3$, $R_4$, $R_5$, $R_6$, $R_7$, $R_8$, $R_9$, $R_{10}$, $R_{11}$, $R_{12}$, and $R_{13}$ is independently selected from H and C1-C6 alkyl;
$R_{14}$ is selected from H, C1-C6 alkyl, $R_{15}C(O)$, and $R_{16}OC(O)$,
$R_{15}$ and $R_{16}$ are independently selected from H and C1-C6 alkyl; and
any alkyl is optionally substituted by one or more halogen.

In some other particular embodiments of a compound of formula (I),
X is CH, Y is N, and Z is C; or X is CH, Y is C, and Z is N; or X is N, Y is N, and Z is C;
ring A is phenyl or 5- or 6-membered heteroaryl having one heteroatom, which heteroatom is selected from N, O and S;
m is 0 or 1;
each $R_1$ is independently selected from halogen, C1-C6 alkyl, $R_2O$, $R_3S(O)_2$, $R_4S(O)_2N(R_5)$, and $R_{13}R_{14}NS(O)_2$;
each one of $R_2$, $R_3$, $R_4$, $R_8$, $R_{13}$ and $R_{14}$ is independently selected from H and C1-C6 alkyl;
and any alkyl is optionally substituted by one or more halogen.

In some other particular embodiments of a compound of formula (I),
X is CH, Y is N, and Z is C; or X is CH, Y is C, and Z is N; or X is N, Y is N, and Z is C;
ring A is phenyl, 2-thienyl, 3-pyridyl, or 4-pyridyl;
m is 0 or 1;
each $R_1$ is independently selected from halogen, C1-C6 alkyl, $R_2O$, $R_3S(O)_2$, $R_4S(O)_2N(R_5)$, and $R_{13}R_{14}NS(O)_2$;
each one of $R_2$, $R_3$, $R_4$, $R_5$, $R_{13}$ and $R_{14}$ is independently selected from H and C1-C6 alkyl;
and any alkyl is optionally substituted by one or more halogen.

In some other particular embodiments of a compound of formula (I),
X is CH, Y is N, and Z is C; or X is CH, Y is C, and Z is N; or X is N, Y is N, and Z is C;
ring A is phenyl, 2-thienyl, 3-pyridyl, or 4-pyridyl;
m is 0 or 1;
each $R_1$ is independently selected from halogen, C1-C3 alkyl, $R_2O$, $R_3S(O)_2$, $R_4S(O)_2N(R_5)$, and $R_{13}R_{14}NS(O)_2$;
each one of $R_2$, $R_3$, $R_4$, $R_5$, $R_{13}$ and $R_{14}$ is independently selected from H and C1-C3 alkyl;
and any alkyl is optionally substituted by one or more halogen.

In some of the above mentioned particular embodiments, X is CH, Y is N, and Z is C. In some other of the above mentioned particular embodiments, X is CH, Y is C, and Z is N. In still other of the above mentioned particular embodiments, X is N, Y is N, and Z is C.

In some of the above mentioned particular embodiments, when ring A is phenyl, m is different from 0.

In some other of the above mentioned particular embodiments, when any alkyl is optionally substituted by one or more halogen, said halogen is F.

In some other of the above mentioned particular embodiments, ring A is 5- or 6-membered heteroaryl. In some of these embodiments, ring A is thienyl, e.g. 2-thienyl. In some other of these embodiments, ring A is a ring of formula (IIa) as defined herein, wherein at least one of $W_1$ and $W_2$ is N.

In some other of the above mentioned particular embodiments, ring A is phenyl or 6-membered heteroaryl.

In some embodiments, the compound is a compound of formula (Id), more particularly a compound of formula (Ig), ring A is 5- or 6-membered heteroaryl, and m is 0 or 1.

In some of these embodiments, the compound is a compound of formula (Ig), ring A is 5- or 6-membered heteroaryl, and m is 0. In some of these embodiments, the compound is a compound of formula (Ig), ring A is 5-membered heteroaryl, and m is 0.

In some other of these embodiments, the compound is a compound of formula (Ig), ring A is 6-membered heteroaryl, and m is 0 or 1. In some of these embodiments, the compound is a compound of formula (Ig), ring A is 6-membered heteroaryl, and m is 0.

In some embodiments, the compound is a compound of formula (Ib), ring A is 5- or 6-membered heteroaryl, and m is 0 or 1. In some of these embodiments, the compound is a compound of formula (Ib), ring A is 5- or 6-membered heteroaryl, and m is 0. In some of these embodiments, the compound is a compound of formula (Ib), ring A is 5-membered heteroaryl, and m is 0. For example, in some embodiments, the compound is a compound of formula (Ib), ring A is 4-pyridyl or 2-thienyl and m is 0. In some embodiments, the compound is a compound of formula (Id), ring A is 4-pyridyl or 2-thienyl and m is 0. In some of these embodiments, the compound is a compound of formula (Ig), ring A is 4-pyridyl or 2-thienyl, and m is 0.

In some other embodiments, the compound is a compound of formula (Ib), (Id) or (Ig), ring A is pyridyl or thienyl, and m is 0 or 1. In some of these embodiments, the compound is a compound of formula (Ig).

In some of the above embodiments, m is 0 when ring A is thienyl.

In some embodiments of a compound of formula (I), ring A is 4-pyridyl, or 2-thienyl, and m is 0; or ring A is phenyl, 3-pyridyl, or 4-pyridyl, and m is 1.

In some embodiments, the moiety of formula (II)

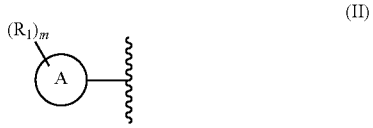

is a moiety selected from

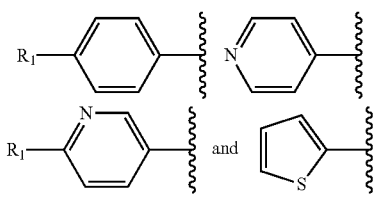

wherein $R_1$ is as defined herein, e.g. $R_1$ is selected from halogen, C1-C6 alkyl, $R_2O$, $R_3S(O)_2$, $R_4S(O)_2N(R_5)$, and $R_{13}R_{14}NS(O)_2$.

In some embodiments, the moiety of formula (II) is selected from phenyl, 4-methoxyphenyl, 4-fluorophenyl, 4-chlorophenyl, 4-methylsulfonylphenyl, 4-sulfamoylphenyl, 4-(methylsulfonamido)phenyl, pyridin-4-yl, 6-methylpyridin-3-yl, 6-trifluoromethylpyridin-3-yl, 6-methoxypyridin-3-yl, and 2-thienyl. In some further embodiments, the moiety of formula (II) is selected from 4-methoxyphenyl, 4-chlorophenyl, 4-methylsulfonylphenyl, 4-sulfamoylphenyl, 4-(methylsulfonamido)phenyl, pyridin-4-yl, 6-methylpyridin-3-yl, 6-methoxypyridin-3-yl, and 2-thienyl.

In some further embodiments,
X is CH or N;
Y is N and Z is C; or Y is C and Z is N;
ring A is phenyl, 3-pyridyl, 4-pyridyl, or 2-thienyl,
m is 0 or 1;
each $R_1$ is independently selected from C1-C6 alkyl, $R_2O$, and $R_3S(O)_2$;
each one of $R_2$ and $R_3$ is independently selected from C1-C6 alkyl; and any alkyl is optionally substituted by one or more halogen, e.g. one or more F.

In still further embodiments,
X is CH or N;
Y is N and Z is C; or Y is C and Z is N;
ring A is phenyl, 3-pyridyl, 4-pyridyl, or 2-thienyl,
m is 0 or 1;
each $R_1$ is independently selected from C1-C3 alkyl, $R_2O$, and $R_3S(O)_2$;
each one of $R_2$ and $R_3$ is independently selected from C1-C3 alkyl; and
any alkyl is optionally substituted by one or more halogen, e.g. one or more F.

In still further embodiments,
X is CH or N;
Y is N and Z is C; or Y is C and Z is N;
ring A is 3-pyridyl, 4-pyridyl, or 2-thienyl,
m is 0 or 1; e.g. m is 0 when ring A is 4-pyridyl or 2-thienyl and m is 1 when ring A is 3-pyridyl;
each $R_1$ is independently selected from C1-C3 alkyl, $R_2O$, and $R_3S(O)_2$;
each one of $R_2$ and $R_3$ is independently selected from C1-C3 alkyl; and
any alkyl is optionally substituted by one or more halogen, e.g. one or more F.

In some further embodiments, e.g. in some embodiments of formula (Ij),
X is CH or N;
Y is N and Z is C; or Y is C and Z is N;
ring A is phenyl, 3-pyridyl, or 4-pyridyl;
m is 0 or 1; e.g. m is 0 when ring A is 4-pyridyl, and m is 1 when ring A is phenyl or 3-pyridyl;
each $R_1$ is independently selected from C1-C6 alkyl, $R_2O$, and $R_3S(O)_2$;
each one of $R_2$ and $R_3$ is independently selected from C1-C6 alkyl; and
any alkyl is optionally substituted by one or more halogen, e.g. one or more F.

In still further embodiments, e.g. in some embodiments of formula (Ij),
X is CH or N;
Y is N and Z is C; or Y is C and Z is N;
ring A is 3-pyridyl or 4-pyridyl;
m is 0 or 1; e.g. m is 0 when ring A is 4-pyridyl, and m is 1 when ring A is 3-pyridyl;
each $R_1$ is independently selected from C1-C3 alkyl, $R_2O$, and $R_3S(O)_2$;
each one of $R_2$ and $R_3$ is independently selected from C1-C6 alkyl; and
any alkyl is optionally substituted by one or more halogen, e.g. one or more F.

In still further embodiments,
X is CH or N;
Y is N and Z is C; or Y is C and Z is N;
ring A is phenyl, 3-pyridyl, 4-pyridyl, or 2-thienyl;
m is 0 or 1;
each $R_1$ is independently selected from methyl, $CH_3O$, and $CH_3S(O)_2$; and any methyl is optionally substituted by one or more F.

In still further embodiments,
X is CH or N;
Y is N and Z is C; or Y is C and Z is N;
ring A is phenyl, 3-pyridyl, 4-pyridyl, or 2-thienyl;
m is 0 or 1;
each $R_1$ is independently selected from methyl, $CH_3O$, and $CH_3S(O)_2$; and any methyl is optionally substituted by one or more F.

In still further embodiments,
X is CH or N;
Y is N and Z is C; or Y is C and Z is N;
ring A is 3-pyridyl, 4-pyridyl or 2-thienyl;
m is 0 or 1;
each $R_1$ is independently selected from methyl, $CH_3O$, and $CH_3S(O)_2$; and any methyl is optionally substituted by one or more F.

In still further embodiments,
X is CH or N;
Y is N and Z is C; or Y is C and Z is N;
ring A is 3-pyridyl or 4-pyridyl;
m is 0 or 1;
each $R_1$ is independently selected from methyl, $CH_3O$, and $CH_3S(O)_2$; and any methyl is optionally substituted by one or more F.

In some of these embodiments, when ring A is 3-pyridyl, 4-pyridyl or phenyl, the moiety (II) is a moiety of formula (IIa).

In some embodiments, when ring A is 3-pyridyl, m is 1 or 2 and one $R_1$ is attached in 6-position on the pyridyl ring.

In still further embodiments, the moiety of formula (II) is 5-membered unsubstituted heteroaryl, e.g. thienyl or furyl, in particular thienyl. In still further embodiments, the moiety of formula (II) is 2-thienyl or 2-furyl, in particular 2-thienyl. In some of these embodiments, the compound of formula (I) is a compound of formula (Id).

The compounds of formula (I) also may be transformed into suitable, pharmaceutically acceptable salts. The term pharmaceutically acceptable salt of a compound refers to a salt that is pharmaceutically acceptable, as defined herein, and that possesses the desired pharmacological activity of the parent compound. Pharmaceutically acceptable salts include acid addition salts formed with inorganic acids, e.g. hydrochloric acid, hydrobromic acid, sulphuric acid, nitric acid, phosphoric acid; or formed with organic acids, e.g. acetic acid, benzenesulfonic acid, benzoic acid, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid, etc.

In the preparation of acid addition salts, preferably such acid are used which form suitably therapeutically acceptable salts. Examples of such acids are hydrohalogen acids, sulfuric acid, phosphoric acid, nitric acid, aliphatic, alicyclic, aromatic or heterocyclic carboxylic or sulfonic acids, such as formic acid, acetic acid, propionic acid, succinic acid, glycolic acid, lactic acid, malic acid, tartaric acid, citric acid, ascorbic acid, maleic acid, hydroxymaleic acid, pyruvic acid, p-hydroxybenzoic acid, embonic acid, methanesulfonic acid, ethanesulfonic acid, hydroxyethanesulfonic acid, halogenbenzenesulfonic acid, toluenesulfonic acid or naphthalenesulfonic acid.

Whenever a chiral atom is present in a chemical structure, it is intended that all stereoisomers associated with that chiral atom are encompassed by the structure, unless otherwise specified. Using the Cahn-Ingold-Prelog RS notational system, any asymmetric atom may be present in the (R)- or (S)-configuration, and the compound may be present as a mixture of its stereoisomers, e.g. a racemic mixture, or one stereoisomer only, each being within the scope of the present invention.

The present invention includes pharmaceutical compositions comprising at least one compound of formula (I), or an individual isomer, racemic or non-racemic mixture of isomers or a pharmaceutically acceptable salt thereof, together with at least one pharmaceutically acceptable excipient, e.g. a carrier, and optionally other therapeutic and/or prophylactic ingredients.

A pharmaceutical composition according to the invention may be for topical (local) or systemic administration, e.g. for enteral administration, such as rectal or oral administration, or for parenteral administration to a mammal (especially a human), and comprises a therapeutically effective amount of a compound according to the invention or a pharmaceutically acceptable salt thereof, as active ingredient, in association with a pharmaceutically acceptable excipient, e.g. a pharmaceutically acceptable carrier. The therapeutically effective amount of the active ingredient is as defined herein and depends e.g. on the species of mammal, the body weight, the age, the individual condition, individual pharmacokinetic data, the disease to be treated and the mode of administration.

For enteral, e.g. oral, administration, the compounds of the invention may be formulated in a wide variety of dosage forms. The pharmaceutical compositions and dosage forms may comprise a compound or compounds of the present invention or pharmaceutically acceptable salt(s) thereof as the active component. The pharmaceutically acceptable carriers may be either solid or liquid. Solid form preparations include powders, tablets, pills, lozenges, capsules, cachets, suppositories, and dispersible granules. A solid carrier may be one or more substances which may also act as diluents, flavouring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The formulation of the active compound may comprise an encapsulating material as carrier, providing a capsule in which the active component, with or without carriers, is surrounded by a carrier, which is in association with it.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well-known suspending agents. Solid form preparations include solutions, suspensions, and emulsions, and may contain, in addition to the active component, colorants, flavors, stabilizers, buffers, artificial and natural sweeteners, dispersants, thickeners, solubilising agents, and the like.

Exemplary compositions for rectal administration include suppositories which can contain, for example, a suitable non-irritating excipient, such as cocoa butter, synthetic glyceride esters or polyethylene glycols, which are solid at ordinary temperatures, but liquefy and/or dissolve in the rectal cavity to release the drug.

The compounds of the invention also may be administered parenterally, e.g. by inhalation, injection or infusion, e.g. by intravenous, intraarterial, intraosseous, intramuscular, intracerebral, intracerebroventricular, intrasynovial, intrasternal, intrathecal, intralesional, intracranial, intracutaneous and subcutaneous injection or infusion. Thus, for parenteral administration, the pharmaceutical compositions of the invention may be in the form of a sterile injectable or infusible preparation, for example, as a sterile aqueous or oleaginous suspension. This suspension may be formulated according to techniques known in the art using suitable dispersing or wetting agents (e.g., Tween 80), and suspending agents. The sterile injectable or infusible preparation may also be a sterile injectable or infusible solution or suspension in a non-toxic parenterally acceptable diluent or solvent. For example, the pharmaceutical composition may be a solution in 1,3-butanediol. Other examples of acceptable vehicles and solvents that may be employed in the compositions of the present invention include, but are not limited to, mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant.

Solutions for parenteral use also may contain suitable stabilizing agents, and if necessary, buffer substances. Suitable stabilizing agents include antioxidizing agents, such as sodium bisulfate, sodium sulfite or ascorbic acid, either alone or combined, citric acid and its salts and sodium EDTA. Parenteral solutions may also contain preservatives, such as benzalkonium chloride, methyl- or propyl-paraben, and chlorobutanol.

For inhalation or nasal administration, suitable pharmaceutical formulations are as particles, aerosols, powders, mists or droplets, e.g. with an average size of about 10 um in diameter or less. For example, compositions for inhalation may be prepared as solutions in saline, employing benzyl alcohol or other suitable preservatives, absorption promoters to enhance bioavailability, fluorocarbons, and/or other solubilising or dispersing agents known in the art.

The pharmaceutical compositions of the invention also may be administered topically, to the skin or to a mucous membrane. For topical application, the pharmaceutical composition may be e.g. a lotion, a gel, a paste, a tincture, a transdermal patch, or a gel for transmucosal delivery.

The composition may be formulated as a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water.

Alternatively, the pharmaceutical composition may be formulated as a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water.

The pharmaceutical compositions of this invention may also be topically applied to the lower intestinal tract by rectal suppository formulation or in a suitable enema formulation.

Suitable pharmaceutical excipients, e.g. carriers, and methods of preparing pharmaceutical dosage forms are described in Remington's Pharmaceutical Sciences, Mack Publishing Company, a standard reference text in art of drug formulation. The pharmaceutical compositions may comprise from approximately 1% to approximately 95%, preferably from approximately 20% to approximately 90% of a compound of the invention, together with at least one pharmaceutically acceptable excipient.

In general, the compounds of the invention will be administered in a therapeutically effective amount by any of the accepted modes of administration for agents that serve similar utilities. Suitable daily dosages typically ranges from 1 to 1000 mg, e.g. 1-500 mg, or 1-50 mg of the compound of formula (I), or an equivalent amount of a pharmaceutically acceptable salt thereof, depending upon numerous factors such as the severity of the disease to be treated, the age and relative health of the patient, the potency of the compound used, the route and form of administration, and the indication towards which the administration is directed, etc. One of ordinary skill in the art of treating such diseases will be able, without undue experimentation and in reliance upon personal knowledge and the disclosure of this application, to ascertain a therapeutically effective amount of the compounds of the present invention for a given disease. Compounds of the invention may be administered as pharmaceutical formulations including those suitable for enteral or parenteral administration. The preferred manner of administration is generally oral using a convenient daily dosage regimen which can be adjusted according to the degree of affliction.

The compounds of the present invention are contemplated as useful for the treatment of diseases caused by RNA viral infection in a mammal, e.g. non-enveloped single-stranded (+) RNA viral infection, in particular diseases caused by picornaviruses, i.e. viruses belonging to the family Picornaviridae. In some embodiments the picornavirus is selected from an enterovirus, a rhinovirus, a hepatovirus, a cardiovirus, an aphthovirus, a poliovirus, a parechovirus, an erbovirus, a kobuvirus, a teschovirus, a coxsackie virus; e.g. from an enterovirus, a rhinovirus, a hepatovirus, a poliovirus, a coxsackie virus. In some embodiments, when the compound of formula (I) is intended for veterinary use, the virus may be selected from an aphthovirus, and a teschovirus.

Diseases that are considered to be linked to, caused by, or otherwise associated with a viral infection, e.g. by a picornavirus, are e.g. pancreatitis, poliomyelitis, encephalitis, meningitis, sepsis, cancer, such as breast, prostate, ovarian and colorectal cancer, paralysis, myocarditis, diabetes, common cold, hand-foot-and-mouth disease, herpangina, pleurodynia, diarrhea, mucocutaneous lesions, respiratory illness, conjunctivitis, myositis, and chronic fatigue syndrome, as well as neurodegenerative diseases such as multiple sclerosis, Parkinson's disease, amyotrophic lateral sclerosis, Alzheimer's disease, and Huntington's disease.

The compounds of the present invention further are contemplated as useful for the treatment of diseases caused by impaired and/or abnormal autophagy. Diseases that are considered to be linked to impaired or abnormal autophagy, are, for example, cancer, cardiac diseases, diabetes, inflammatory diseases, neuropsychiatric diseases, and neurodegenerative diseases such as multiple sclerosis, Parkinson's disease, amyotrophic lateral sclerosis, Alzheimer's disease, and Huntington's disease.

The compound of the present invention is a PI4 kinase inhibitor and as such it is considered as capable of having a usefulness in the treatment of various conditions where inhibition of a PI4 kinase is considered beneficial, e.g. a condition selected from e.g. pancreatitis, poliomyelitis, encephalitis, meningitis, sepsis, cancer, such as breast, prostate, ovarian and colorectal cancer, paralysis, cardiac diseases, such as myocarditis, diabetes, common cold, hand-foot-and-mouth disease, herpangina, pleurodynia, diarrhea, mucocutaneous lesions, respiratory illness, conjunctivitis, myositis, chronic fatigue syndrome, neuropsychiatric diseases, neurodegenerative diseases such as multiple sclerosis, Parkinson's disease, amyotrophic lateral sclerosis, Alzheimer's disease, and Huntington's disease, and inflammatory conditions.

The present invention consequently includes a compound of formula (I) for use in the treatment of any of the above mentioned diseases; a pharmaceutical composition for use in the treatment of any of the above mentioned diseases; the use of a compound of formula (I) in the manufacturing of a medicament for the treatment of any of the above mentioned diseases; and a method of treatment of any of the above mentioned diseases, by administering a compound of formula (I) to an animal or human in need of such treatment. Preferably, the compound of formula (I) is used for the treatment of a human patient. In some embodiments, however, the compound of formula (I) is used for the treatment of an animal (i.e. non-human patient), such as an animal as mentioned herein.

Compounds of the invention may be prepared by the person of ordinary skill in the art using his knowledge within the field of chemical synthesis, in light of the illustrating non-limiting examples that will follow herein below and by referring to the literature within the field.

EXAMPLES

Compounds of the invention were synthesized by following the General Procedures 1-3, described herein below. Their structural formulas and chemical names are given in Table 1.

TABLE 1

| Ex. | Structural formula | Chemical name |
| --- | --- | --- |
| 1 | | 3-(1,3-dimethyl-1H-indazol-5-yl)-2,6-dimethyl-N-(pyridin-4-ylmethyl)imidazo[1,2-b]pyridazin-8-amine |
| 2 | | 3-(1,3-dimethyl-1H-indazol-5-yl)-2,6-dimethyl-N-((6-methylpyridin-3-yl)methyl)imidazo[1,2-b]pyridazin-8-amine |
| 3 | | N-(4-chlorobenzyl)-3-(1,3-dimethyl-1H-indazol-5-yl)-2,6-dimethylimidazo[1,2-b]pyridazin-8-amine |
| 4 | | 3-(1,3-dimethyl-1H-indazol-5-yl)-N-((6-methoxypyridin-3-yl)methyl)-2,6-dimethylimidazo[1,2-b]pyridazin-8-amine |
| 5 | | 3-(1,3-dimethyl-1H-indazol-5-yl)-2,6-dimethyl-N-(thiophen-2-ylmethyl)imidazo[1,2-b]pyridazin-8-amine |

TABLE 1-continued

| Ex. | Structural formula | Chemical name |
| --- | --- | --- |
| 6 | | 3-(1,3-dimethyl-1H-indazol-5-yl)-N-(4-methoxybenzyl)-2,6-dimethylimidazo[1,2-b]pyridazin-8-amine |
| 7 | | 3-(1,3-dimethyl-1H-indazol-5-yl)-2,6-dimethyl-N-(4-(methylsulfonyl)benzyl)imidazo[1,2-b]pyridazin-8-amine |
| 8 | | 3-(1,3-dimethyl-1H-indazol-5-yl)-2,5-dimethyl-N-(pyridin-4-ylmethyl)pyrazolo[1,5-a]pyrimidin-7-amine |
| 9 | | 3-(1,3-dimethyl-1H-indazol-5-yl)-2,5-dimethyl-N-((6-methylpyridin-3-yl)methyl)pyrazolo[1,5-a]pyrimidin-7-amine |
| 10 | | 3-(1,3-dimethyl-1H-indazol-5-yl)-N-(4-methoxybenzyl)-2,5-dimethylpyrazolo[1,5-a]pyrimidin-7-amine |
| 11 | | N-(4-chlorobenzyl)-3-(1,3-dimethyl-1H-indazol-5-yl)-2,5-dimethylpyrazolo[1,5-a]pyrimidin-7-amine |

TABLE 1-continued

| Ex. | Structural formula | Chemical name |
|---|---|---|
| 12 | | 3-(1,3-dimethyl-1H-indazol-5-yl)-2,5-dimethyl-N-(4-(methyl-sulfonyl)benzyl)pyrazolo[1,5-a]pyrimidin-7-amine |
| 13 | | 4-(((3-(1,3-dimethyl-1H-indazol-5-yl)-2,5-dimethylpyrazolo[1,5-a]pyrimidin-7-yl)amino)methyl)benzene-sulfonamide |
| 14 | | 3-(1,3-dimethyl-1H-indazol-5-yl)-N-((6-methoxypyridin-3-yl)methyl)-2,5-dimethylpyrazolo[1,5-a]pyrimidin-7-amine |
| 15 | | 3-(1,3-dimethyl-1H-indazol-5-yl)-2,5-dimethyl-N-(thiophen-2-ylmethyl)pyrazolo[1,5-a]pyrimidin-7-amine |
| 16 | | N-(4-(((3-(1,3-dimethyl-1H-indazol-5-yl)-2,5-dimethylpyrazolo[1,5-a]pyrimidin-7-yl)amino)methyl)phenyl)methane-sulfonamide |
| 17 | | 3-(1,3-dimethyl-1H-indazol-5-yl)-2,5-dimethyl-N-((6-trifluoromethylpyridin-3-yl)methyl)pyrazolo[1,5-a]pyrimidin-7-amine |

TABLE 1-continued

| Ex. | Structural formula | Chemical name |
|---|---|---|
| 18 | | N-(benzyl)-3-(1,3-dimethyl-1H-indazol-5-yl)-2,5-dimethylpyrazolo[1,5-a]pyrimidin-7-amine |
| 19 | | N-(4-fluorobenzyl)-3-(1,3-dimethyl-1H-indazol-5-yl)-2,5-dimethylpyrazolo[1,5-a]pyrimidin-7-amine |
| 20 | | 8-(1,3-dimethyl-1H-indazol-5-yl)-2,7-dimethyl-N-(pyridin-4-ylmethyl)pyrazolo[1,5-a][1,3,5]triazin-4-amine |
| 21 | | 8-(1,3-dimethyl-1H-indazol-5-yl)-N-(4-methoxybenzyl)-2,7-dimethylpyrazolo[1,5-a][1,3,5]triazin-4-amine |
| 22 | | 8-(1,3-dimethyl-1H-indazol-5-yl)-2,7-dimethyl-N-((6-methylpyridin-3-yl)methyl)pyrazolo[1,5-a][1,3,5]triazin-4-amine |
| 23 | | 4-(((8-(1,3-dimethyl-1H-indazol-5-yl)-2,7-dimethylpyrazolo[1,5-a][1,3,5]triazin-4-yl)amino)methyl)benzenesulfonamide |

TABLE 1-continued

| Ex. | Structural formula | Chemical name |
|---|---|---|
| 24 | | N-(4-chlorobenzyl)-8-(1,3-dimethyl-1H-indazol-5-yl)-2,7-dimethylpyrazolo[1,5-a][1,3,5]triazin-4-amine |
| 25 | | 8-(1,3-dimethyl-1H-indazol-5-yl)-2,7-dimethyl-N-(4-(methylsulfonyl)benzyl)pyrazolo[1,5-a][1,3,5]triazin-4-amine |
| 26 | | N-(4-(((8-(1,3-dimethyl-1H-indazol-5-yl)-2,7-dimethylpyrazolo[1,5-a][1,3,5]triazin-4-yl)amino)methyl)phenyl)methanesulfonamide |
| 27 | | 8-(1,3-dimethyl-1H-indazol-5-yl)-2,7-dimethyl-N-(thiophen-2-ylmethyl)pyrazolo[1,5-a][1,3,5]triazin-4-amine |
| 28 | | 8-(1,3-dimethyl-1H-indazol-5-yl)-N-((6-methoxypyridin-3-yl)methyl)-2,7-dimethylpyrazolo[1,5-a][1,3,5]triazin-4-amine |

General Procedures:

Reactions were performed in flame-dried sealed tubes or oven-dried glassware under a positive pressure of argon or nitrogen, unless otherwise noted. Air- and moisture-sensitive liquids and solutions were transferred via syringe. Diethyl ether (Et$_2$O) and tetrahydrofuran (THF) were distilled from sodium/benzophenone-ketyl. Dichloromethane (CH$_2$Cl$_2$) was distilled from calcium hydride. All other chemicals were obtained from commercial vendors and were used without further purification unless noted otherwise. Molecular sieves were activated at 350° C. and were crushed immediately prior to use, then flame-dried under vacuum. Reactions were monitored by thin layer chromatography (TLC) with 0.25-mm E. Merck pre-coated silica gel plates. Organic solutions were concentrated by rotary evaporation below 50° C. Flash column chromatography was performed employing 60-120 and 230-400 mesh silica gel. Yields refer to chromatographically and spectroscopically pure compounds unless otherwise noted. $^1$H and $^{13}$C spectra were recorded on a Bruker AVANCE III HD 400 MHz spectrometer. Chemical shifts are expressed in parts per million (δ scale) downfield from tetramethylsilane and are referenced to the residual resonance in the NMR solvent (CHCl$_3$: δ 7.26 for $^1$H NMR, δ 77.16 for $^{13}$C NMR). LC-MS was performed on an Agilent XCT Ion Trap equipped with chemstation and Bruker daltonics software.

In the context of the General Procedures 1-3, described herein below, the term $R_4NH_2$ refers to an amine of the general formula (III)

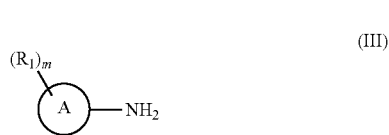

wherein m, $R_1$, and ring A are as described herein.

Tetramethyl-[1,3,2]dioxaborolan-2-yl)-1H-indazole, used in the General Procedures 1-3, was synthesized by the below 2-step procedure illustrated in the following reaction scheme:

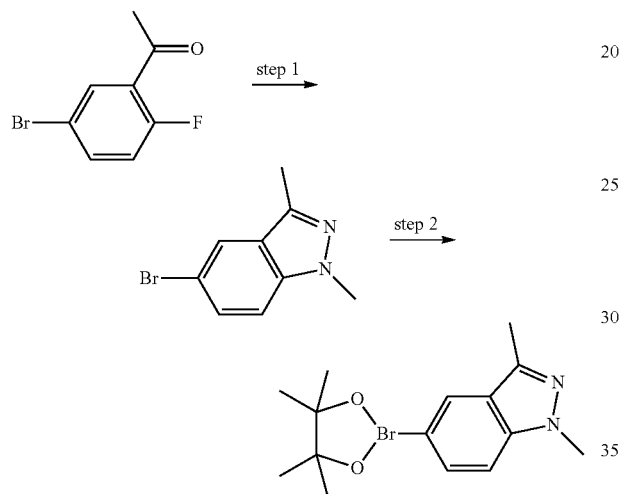

Step 1

To a stirred solution of 1-(5-bromo-2-fluoro-phenyl)-ethanone (10.0 g, 0.046 mol) in pyridine (50 mL) was added methyl hydrazine (2.7 mL, 0.050 mol) at room temperature. The resulting reaction mass was stirred at 100° C. for 16 hours. The crude product obtained after complete evaporation of the volatiles was diluted with water (50 mL) and extracted with ethyl acetate (100 mL*2). The organic layers were combined, dried over anhydrous sodium sulphate and concentrated under reduced pressure to obtain the product as a pale yellow solid. The crude product was purified by silica gel (230-400) column chromatography (15% ethyl acetate in hexane) to obtain 5-bromo-1,3-dimethyl-1H-indazole as a pale yellow oil (5.4 g, 52.4%).

Step 2

To a stirred solution of 5-bromo-1,3-dimethyl-1H-indazole (5.4 g, 0.023 mol) and 4,4,5,5,4',4',5',5'-octamethyl-[2,2']bi[[1,3,2]dioxaborolanyl] (7.3 g. 0.0287 mol) in dioxane (54 mL, 10 V) were added potassium acetate (7.05 g, 0.0719 mol) and palladium tetrakis (1.38 g, 0.0011 mol) under room temperature. The resulting reaction mass was stirred at 100° C. over a period of 3 hours. The reaction was monitored by TLC. The reaction mass was diluted with ethyl acetate (200 mL) and filtered through a celite pad. The organic layer was washed with water (500 mL), brine (250 mL), dried over anhydrous sodium sulphate and concentrated. The crude product obtained was purified by silica gel (230-400) column chromatography (15% ethyl acetate in hexane) to obtain tetramethyl-[1,3,2]dioxaborolan-2-yl)-1H-indazole as an off-white solid (5.2 g, 80%).

General Procedure 1: Synthesis of Imidazopyridazine Derivatives (Scheme 1)

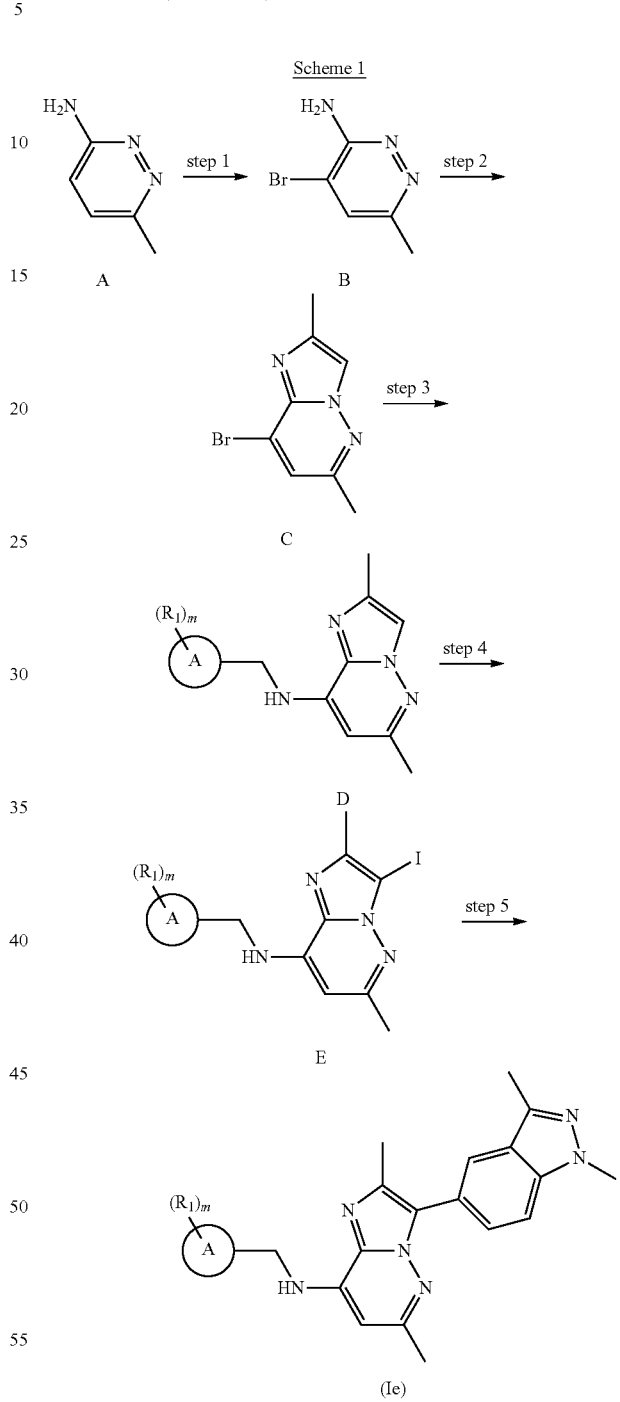

Step 1

To a solution of 6-methyl-pyridazin-3-ylamine, A (2.0 g, 0.018 mol) in acetonitrile (60 mL, 30 V) was added N-bromo succinamide (3.92 g, 0.022 mol) under room temperature. The reaction mass was stirred at room temperature for 2 hours. The reaction was monitored by TLC. The crude reaction mass obtained upon evaporation of the volatiles was purified by silica gel (60-120) column chromatography (3% methanol in dichloromethane) to obtain 4-bromo-6-methyl-pyridazin-3-ylamine, B, (0.6 g, 30%) as a dark brown solid.

Step 2

To a solution of B (0.6 g, 3.1 mmol) in ethanol (6 mL, 10 V) was added chloro acetone (0.4 mL, 4.4 mmol) under room temperature. The resulting reaction mass was stirred at reflux temperature for 16 hours. The reaction was monitored by TLC. The crude reaction mass obtained upon evaporation of the volatiles was basified with saturated sodium bicarbonate and extracted with dichloromethane (100 mL). The organic layer was separated, dried over anhydrous sodium sulphate and concentrated under reduced pressure. The crude product obtained was purified by silica gel (230-400) column chromatography (1.5% methanol in dichloromethane) to obtain 8-bromo-2,6-dimethyl-imidazo[1,2-b]pyridazine, C, (0.15 g, 20%) as a pale yellow solid.

Step 3

To a solution of C (0.33 g, 1.4 mmol) and amine $R_4NH_2$ (0.0027 mol, 1.3 eq) in toluene (10 mL, 30 V) under argon atmosphere in a sealed tube were added cesium carbonate (1.0 g, 2.9 mmol) and BINAP (46 mg, 0.07 mmol) at room temperature. The resulting reaction mass was degassed for 5 minutes, palladium acetate (17 mg, 0.07 mmol) was added and stirring was continued at 100° C. for a period of 16 hours. The resulting reaction mass was diluted with ethyl acetate (100 mL) and filtered through celite pad. The ethyl acetate layer was washed with water (50 mL) and brine (50 mL). The organic layer was dried over anhydrous sodium sulphate, filtered and concentrated under reduced pressure. The crude product obtained was purified by silica gel (230-400) column chromatography (3% methanol in dichloromethane) to obtain compound D.

Step 4

To a stirred solution of compound D (1.0 eq) in acetonitrile (10 mL, 10 V) was added N-iodo succinamide (0.9 eq) under ice temperature. The resulting reaction mass was stirred at ice temperature over a period of 10 minutes. The reaction was monitored by TLC. The crude product obtained upon evaporation of the volatiles was purified by silica gel (230-400) column chromatography (3% methanol in dichloromethane) to obtain compound E.

Step 5

To a stirred solution of compound E (1.0 eq) and 1,3-dimethyl-5-(4,4,5,5-tetramethyl-[1,3,2]dioxaborolan-2-yl)-1H-indazole (1.3 eq) in dioxane:water (6 mL, 30 V) were added potassium carbonate (2.5 eq) and $PdCl_2(dppf)DCM$ (0.1 eq) under room temperature. The resulting reaction mass was stirred at 90° C. over a period of 6 hours. The reaction was monitored by TLC. The reaction mass was diluted with ethyl acetate (200 mL) and filtered through celite pad. The organic layer was washed with water (100 mL), brine (50 mL), dried over anhydrous sodium sulphate and concentrated. The crude product obtained was purified by silica gel (230-400) column chromatography (6% methanol in dichloromethane) to obtain a compound of formula (Ie).

The compounds of Examples 1 to 7 were synthesized by following the General Procedure 1, using the appropriate amines of formula (III). The analytical data of the compounds of Examples 1 to 7 are represented in Table 2.

TABLE 2

| Ex. | Analytical Data |
|---|---|
| 1 | $^1$H-NMR (CDCl$_3$, 400 MHz): δ 8.61 (d, 2H), 7.91 (s, 1H), 7.69 (d, 1H), 7.45 (d, 1H), 7.32 (d, 1H), 7.27 (s, 1H), 6.31 (bs, 1H), 5.74 (s, 1H), 4.59 (d, 2H), 4.05 (s, 3H), 2.60 (s, 3H), 2.55 (s, 3H), 2.35 (s, 3H), LCMS: 398.3 [M + H], HPLC purity: 99.25% |
| 2 | $^1$H-NMR (CDCl$_3$, 400 MHz): δ 8.56 (d, 1H), 8.32 (s, 1H), 8.16 (d, 1H), 7.86 (d, 1H), 7.69 (d, 1H), 7.62 (d, 1H), 7.45 (d, 1H), 7.13 (d, 1H), 5.91 (s, 1H), 4.57 (d, 2H), 4.05 (s, 3H), 2.60 (s, 3H), 2.57 (s, 3H), 2.55 (s, 3H), 2.37 (s, 3H), LCMS: 412.3 [M + H], HPLC purity: 99.98% |
| 3 | $^1$H-NMR (CDCl$_3$, 400 MHz): δ 7.90 (s, 1H), 7.70 (d, 1H), 7.45 (d, 1H), 7.32 (m, 4H), 6.10 (bs, 1H), 5.81 (s, 1H), 4.52 (d, 2H), 4.05 (s, 3H), 2.60 (s, 3H), 2.53 (s, 3H), 2.37 (s, 3H), LCMS: 431.6 [M + H], HPLC purity: 99.67% |
| 4 | $^1$H-NMR (CDCl$_3$, 400 MHz): δ 8.20 (d, 1H), 7.89 (s, 1H), 7.67 (d, 1H), 7.62 (d, 1H), 7.44 (d, 1H), 6.76 (d, 1H), 6.31 (s, 1H), 5.90 (s, 1H), 4.47 (d, 2H), 4.05 (s, 3H), 3.95 (s, 3H), 2.61 (s, 3H), 2.52 (s, 3H), 2.39 (s, 3H), LCMS: 428.6 [M + H], HPLC purity: 99.23% |
| 5 | $^1$H-NMR (CDCl$_3$, 400 MHz): δ 7.89 (s, 1H), 7.68 (d, 1H), 7.46 (d, 1H), 7.27 (d, 1H), 7.10 (d, 1H), 7.00 (d, 1H) 6.41 (bs, 1H), 5.99 (s, 1H), 4.72 (d, 2H), 4.05 (s, 3H), 2.61 (s, 3H), 2.54 (s, 3H), 2.41 (s, 3H), LCMS: 403.6 [M + H], HPLC purity: 97.48% |
| 6 | $^1$H-NMR (CDCl$_3$, 400 MHz): δ 7.90 (s, 1H), 7.68 (d, 1H), 7.44 (d, 1H), 7.32 (d, 2H), 6.90 (d, 2H), 6.30 (bs, 1H), 5.91 (s, 1H), 4.47 (d, 2H), 4.05 (s, 3H), 3.83 (s, 3H), 2.60 (s, 3H), 2.53 (s, 3H), 2.38 (s, 3H), LCMS: 427.6 [M + H], HPLC purity: 98.49% |
| 7 | $^1$H-NMR (CDCl$_3$, 400 MHz): δ 8.02 (m, 2H), 7.90 (s, 1H), 7.82 (d, 1H), 7.75 (d, 1H), 7.62 (m, 3H), 5.98 (s, 1H), 4.64 (d, 2H), 3.99 (s, 3H), 3.20 (s, 3H), 2.50 (s, 3H), 2.43 (s, 3H), 2.22 (s, 3H), LCMS: 475.2 [M + H], HPLC purity: 95.44% |

General Procedure 2: Synthesis of Pyrazolopyrimidine Derivatives (Scheme 2)

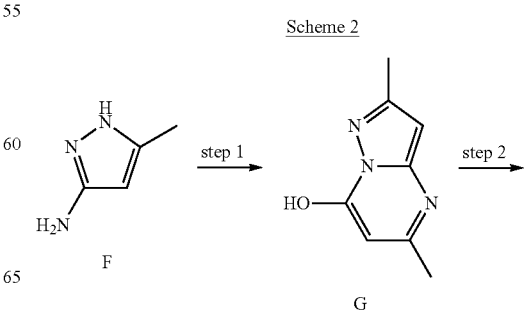

Scheme 2

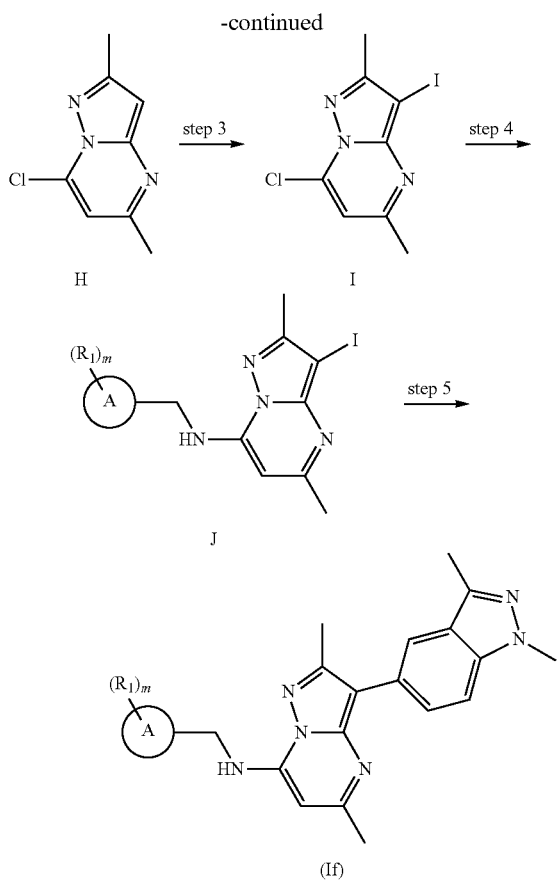

Step 1

To a stirred solution of 5-methyl-1H-pyrazol-3-ylamine, F, (7.0 g, 0.0720 mol), and 3-oxo-butyric acid ethyl ester (11.26 mL, 0.0804 mol) in dioxane (70 mL, 10 V) was added acetic acid (2.1 mL, 0.3 V) under room temperature. The resulting reaction mass was stirred at room temperature for 16 hours. The reaction was monitored by TLC. After complete consumption of the starting material, the reaction mass was filtered, and the residue obtained was suspended in diethyl ether (70 mL) and filtered. The product was dried under high vacuum to obtain 2,5-dimethyl-pyrazolo[1,5-a]pyrimidin-7-ol, G, as a white solid (8.2 g, 69.7%)

Step 2

To a stirred suspension of compound G (4.0 g, 0.0245 mol), in acetonitrile (40 mL, 10 V) was added phosphorous oxy chloride (4.7 mL, 0.049 mol) at room temperature. The resulting reaction mass was stirred at 90° C. over a period of 16 hours. Starting material consumption was monitored by TLC. The reaction mass was added to ice cold water (50 mL), basified with saturated sodium bicarbonate solution, and extracted with ethyl acetate (200 mL*2). The combined organics were dried over anhydrous sodium sulphate, filtered and concentrated under reduced pressure. The crude product was purified by silica gel (230-400) column chromatography (3% methanol in dichloromethane) to obtain 7-chloro-2,5-dimethyl-pyrazolo[1,5-a]pyrimidine, H, as an off-white solid (3.0 g, 68%).

Step 3

To a stirred suspension of compound H (1.5 g, 0.008 mol) in acetonitrile (15 mL, 10 V) was added N-iodo succinamide (1.85 g, 0.008 mol) under ice temperature. The resulting reaction mass was stirred at ice temperature over a period of 10 minutes. The reaction was monitored by TLC. The crude reaction mass was concentrated and purified by silica gel (230-400) column chromatography (3% methanol in dichloromethane) to obtain 7-chloro-3-iodo-2,5-dimethyl-pyrazolo[1,5-a]pyrimidine, I, as an off-white solid (2.3 g, 92%).

Step 4

To a stirred solution of compound I (0.6 g, 1.9 mmol) in ethanol (12 mL, 20 V) were added N,N-diisopropyl ethylamine (0.72 mL, 3.9 mmol) and the amine $R_4NH_2$ (1.3 eq) at RT. The reaction mass was stirred at 70° C. for 16 hours. Starting material consumption was monitored by TLC. After complete evaporation of the volatiles the crude product was diluted with ethyl acetate (200 mL), washed with water (100 mL), dried over anhydrous sodium sulphate, filtered and concentrated under reduced pressure. The crude product was purified by silica gel (230-400) column chromatography (3% methanol in dichloromethane) to obtain the compound J.

Step 5

To a stirred solution of compound J (1.0 eq) and 1,3-dimethyl-5-(4,4,5,5-tetramethyl-[1,3,2]dioxaborolan-2-yl)-1H-indazole (1.3 eq) in dioxane:water (10 mL, 20 V) were added potassium carbonate (2.5 eq) and $PdCl_2$(dppf)DCM (0.1 eq) under room temperature. The resulting reaction mass was stirred at 90° C. over a period of 16 hours. The reaction was monitored by TLC. The reaction mass was diluted with ethyl acetate (200 mL) and filtered through celite pad. The organic layer was washed with water (100 mL), brine (50 mL), dried over anhydrous sodium sulphate and concentrated. The crude product was purified by silica gel (230-400) column chromatography (6% methanol in dichloromethane) to obtain a compound of formula (If).

The compounds of Examples 8 to 19 were synthesized by following the General Procedure 2, using the appropriate amines of formula (III).

Analytical data of the compounds of Examples 8 to 19 are represented in Table 3.

TABLE 3

| Ex. | Analytical Data |
|---|---|
| 8 | $^1$H-NMR (DMSO, 400 MHz): δ 8.52 (m, 3H), 7.85 (s, 1H), 7.75 (d, 1H), 7.59 (d, 1H), 7.37 (d, 2H), 5.96 (s, 1H), 4.65 (d, 2H), 3.97 (s, 3H), 2.56 (s, 3H), 2.50 (s, 3H), 2.31 (s, 3H), LCMS: 398.2 [M + H], HPLC purity: 94.47% |
| 9 | $^1$H-NMR (DMSO, 400 MHz): δ 8.53 (s, 1H), 8.41 (s, 1H), 7.84 (s, 1H), 7.73 (dd, 2H), 7.59 (d, 1H), 7.21 (d, 1H), 6.02 (s, 1H), 4.58 (d, 2H), 3.97 (s, 3H), 2.54 (s, 3H), 2.49 (s, 3H), 2.43 (s, 3H), 2.34 (s, 3H), LCMS: 412.3 [M + H], HPLC purity: 99.86% |
| 10 | $^1$H-NMR (DMSO, 400 MHz): δ 8.38 (t, 1H), 7.84 (s, 1H), 7.75 (d, 1H), 7.58 (d, 1H), 7.35 (d, 2H), 6.90 (d, 2H), 6.00 (s, 1H), 4.52 (d, 2H), 3.97 (s, 3H), 2.54 (s, 3H), 2.50 (s, 3H), 2.32 (s, 3H), LCMS: 427.3 [M + H], HPLC purity: 99.74% |
| 11 | $^1$H-NMR (DMSO, 400 MHz): δ 8.48 (t, 1H), 7.85 (s, 1H), 7.75 (d, 1H), 7.58 (d, 1H), 7.40 (m, 4H), 5.99 (s, 1H), 4.60 (d, 2H), 3.97 (s, 3H), 2.55 (s, 3H), 2.52 (s, 3H), 2.32 (s, 3H), LCMS: 431.3 [M + H], HPLC purity: 99.92% |

TABLE 3-continued

Ex. Analytical Data

12  $^1$H-NMR (CDCl$_3$, 400 MHz): δ 8.00 (s, 1H), 7.94 (d, 1H), 7.87 (d, 1H), 7.70 (dd, 2H), 7.60 (dd, 1H), 7.4 (d, 1H) 6.74 (bs, 1H), 4.72 (d, 2H), 4.03 (s, 3H), 3.08 (s, 3H), 2.60 (s, 3H), 2.58 (s, 3H), 2.45 (s, 3H), LCMS: 475.3 [M + H], HPLC purity: 99.79%
13  $^1$H-NMR (CDCl$_3$, 400 MHz): δ 7.85 (m, 3H), 7.69 (d, 1H), 7.51 (d, 2H), 7.41 (d, 1H), 7.15 (br, 1H), 5.80 (s, 1H), 4.86 (s, 2H), 4.70 (d, 2H), 4.04 (s, 3H), 2.61 (s, 3H), 2.57 (s, 3H), 2.51 (s, 3H), LCMS: 476.2 [M + H], HPLC purity: 99.86%
14  $^1$H-NMR (CDCl$_3$, 400 MHz): δ 8.21 (d, 1H), 7.87 (s, 1H), 7.73 (d, 1H), 7.63 (d, 1H), 7.40 (d, 1H), 6.79 (d, 2H), 6.52 (s, 1H), 5.86 (s, 1H), 4.54 (d, 2H), 4.02 (s, 3H), 3.96 (s, 3H), 2.60 (s, 3H), 2.57 (s, 3H), 2.51 (s, 3H), LCMS: 428.3 [M + H], HPLC purity: 99.67%
15  $^1$H-NMR (CDCl$_3$, 400 MHz): δ 7.87 (s, 1H), 7.72 (d, 1H), 7.40 (d, 1H), 7.30 (d, 1H), 7.11 (d, 1H), 7.02 (d, 1H), 6.67 (bs, 1H), 5.92 (s, 1H), 4.80 (d, 2H), 4.02 (s, 3H), 2.60 (s, 3H), 2.57 (s, 3H), 2.55 (s, 3H), LCMS: 403.0 [M + H], HPLC purity: 99.76%
16  $^1$H-NMR (DMSO, 400 MHz): δ 9.71 (s, 1H), 8.41 (t, 1H), 7.85 (s, 1H), 7.75 (d, 1H), 7.58 (d, 1H), 7.38 (d, 2H), 7.17 (d, 2H), 6.00 (s, 1H), 4.54 (d, 2H), 3.97 (s, 3H), 2.96 (s, 3H), 2.54 (s, 3H), 2.32 (s, 3H), LCMS: 490.6 [M + H], HPLC purity: 99.92%
17  $^1$H-NMR (DMSO, 400 MHz): δ 8.86 (s, 1H), 8.58 (t, 1H), 8.08 (d, 1H), 7.89 (d, 1H), 7.858 (s, 1H), 7.73 (d, 1H), 7.58 (d, 1H), 6.12 (s, 1H), 4.76 (d, 2H), 3.97 (s, 3H), 2.56 (s, 3H), 2.50 (s, 3H), 2.32 (s, 3H), LCMS: 466.6 [M + H], HPLC purity: 99.40%
18  $^1$H-NMR (DMSO, 400 MHz): δ 8.44 (t, 1H), 7.85 (d, 1H), 7.77 (d, 1H), 7.58 (d, 1H), 7.41 (d, 2H), 7.34 (m, 2H), 7.25 (m, 1H), 5.99 (s, 1H), 4.60 (d, 2H), 3.97 (s, 3H), 2.55 (s, 3H), 2.50 (s, 3H), 2.31 (s, 3H), LCMS: 397.6 [M + H], HPLC purity: 99.80%
19  $^1$H-NMR (DMSO, 400 MHz): δ 8.44 (t, 1H), 7.82 (s, 1H), 7.71 (d, 1H), 7.54 (d, 1H), 7.44 (dd, 12H), 7.14 (m, 2H), 5.99 (s, 1H), 4.56 (d, 2H), 3.974 (s, 3H), 2.50 (s, 3H), 2.47 (s, 3H), 2.30 (s, 3H), LCMS: 415.7 [M + H], HPLC purity: 97.53%

General Procedure 3: Synthesis of Pyrazolo Triazine Derivatives (Scheme 3)

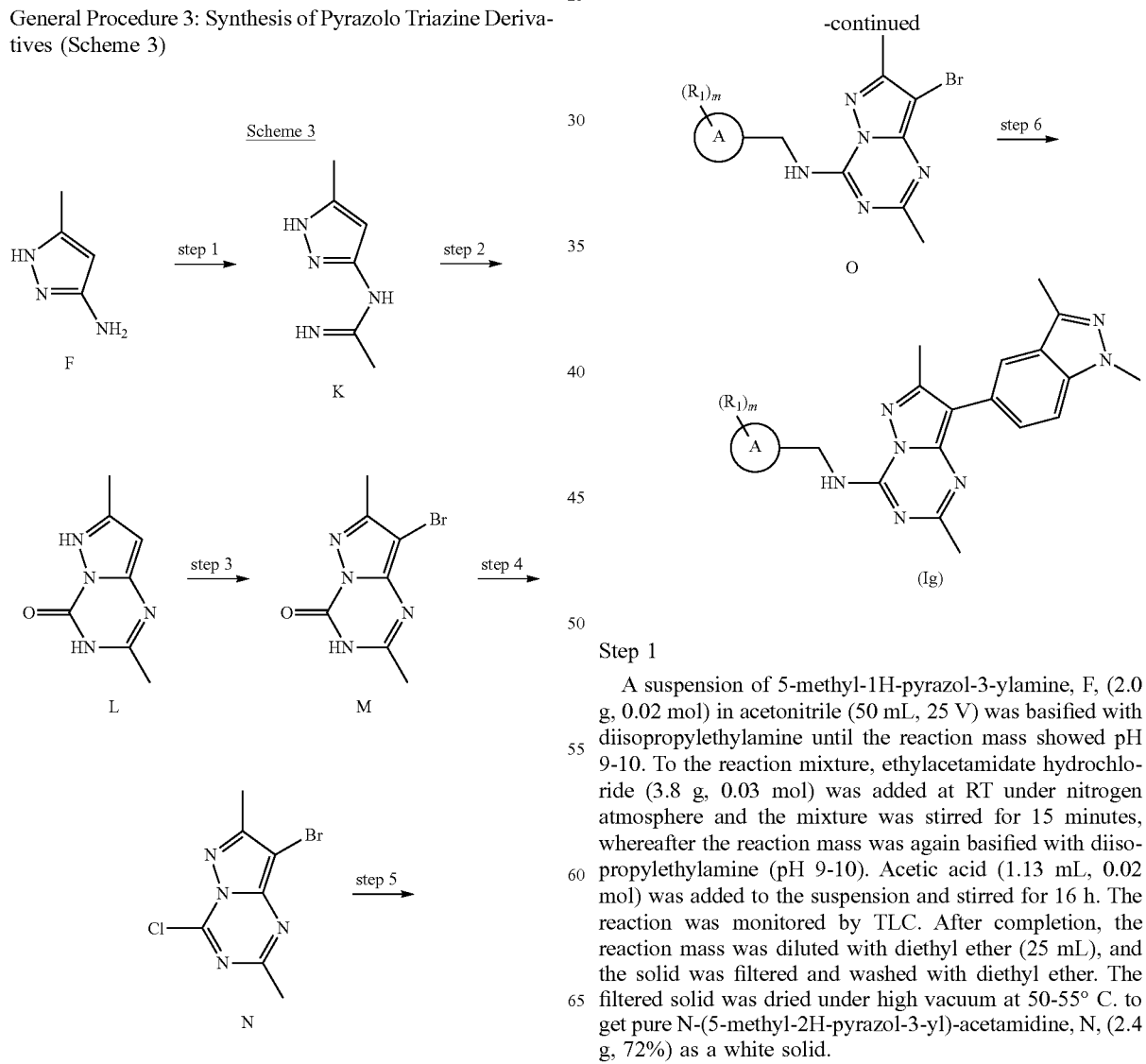

Step 1

A suspension of 5-methyl-1H-pyrazol-3-ylamine, F, (2.0 g, 0.02 mol) in acetonitrile (50 mL, 25 V) was basified with diisopropylethylamine until the reaction mass showed pH 9-10. To the reaction mixture, ethylacetamidate hydrochloride (3.8 g, 0.03 mol) was added at RT under nitrogen atmosphere and the mixture was stirred for 15 minutes, whereafter the reaction mass was again basified with diisopropylethylamine (pH 9-10). Acetic acid (1.13 mL, 0.02 mol) was added to the suspension and stirred for 16 h. The reaction was monitored by TLC. After completion, the reaction mass was diluted with diethyl ether (25 mL), and the solid was filtered and washed with diethyl ether. The filtered solid was dried under high vacuum at 50-55° C. to get pure N-(5-methyl-2H-pyrazol-3-yl)-acetamidine, N, (2.4 g, 72%) as a white solid.

Step 2

To a solution of sodium metal (2.74 g, 0.12 mol) in ethanol (23 mL, 30 V) under nitrogen atmosphere was added N (3.3 g, 0.02 mol) and diethyl carbonate (23 mL, 0.2 mol) at room temperature. The resulting reaction mass was refluxed for 16 h. The progress of the reaction was monitored by TLC. After completion, the reaction mass was cooled to room temperature and resultant mass was concentrated under reduced pressure at 50-55° C. to remove ethanol. The crude product obtained upon evaporation of the volatiles were diluted with water and acidified with acetic acid (pH: 4-5). The aqueous layer was extracted with dichloromethane (400 mL*3), the organic layers were combined, dried over anhydrous sodium sulphate, filtered and concentrated under reduced pressure. The solid product was washed with minimum volumes of acetonitrile, filtered and dried to get pure 2,7-dimethyl-3H-pyrazolo[1,5-a][1,3,5]triazin-4-one, L, (1.6 g, 40%) as an off-white solid.

Step 3

To a stirred solution of compound L (1.0 g, 0.006 mol) in acetonitrile (10 mL, 10 V) was added N-bromo succinamide (1.3 g, 0.007 mol) under ice temperature. The resulting reaction mass was stirred at ice temperature over a period of 1 hour. The reaction was monitored by TLC. The precipitate formed was filtered through buchner funnel, washed with minimum amount of acetonitrile and dried to obtain 8-bromo-2,7-dimethyl-3H-pyrazolo[1,5-a][1,3,5]triazin-4-one, M, (0.7 g, 50%) as a white solid.

Step 4

To a solution of compound M (0.2 g, 0.8 mmol) in toluene (5 mL, 25 V) were added diisopropylethylamine (0.3 mL, 1.6 mmol) and phosphorous oxy chloride (2.0 mL, 0.02 mol) at room temperature. The resulting reaction mass was stirred at reflux temperature for 16 hours. The crude product obtained upon evaporation of the volatiles was stripped with toluene (10 mL*2) and the 8-bromo-4-chloro-2,7-dimethyl-pyrazolo[1,5-a][1,3,5]triazine, N, obtained was taken to next step without further purification and characterization.

Step 5

The crude compound N (0.2 g, 0.7 mmol), obtained upon evaporation of volatiles, was dissolved in THF (5 mL, 25 V). Diisopropylethylamine (0.3 mL, 1.5 mmol) and the amine $R_4NH_2$ (1.2 eq) were added at ice temperature, and the resulting reaction mass was stirred at room temperature for 1 hour. The reaction was monitored by TLC. The reaction mass was diluted with dichloromethane (100 mL), washed with water (50 mL*2) and brine solution (50 mL*2). The organic layer was separated, dried over anhydrous sodium sulphate, filtered and concentrated under reduced pressure. The crude product was purified by silica gel (230-400) column chromatography (10% ethyl acetate in hexane) to obtain compound 0 (120 mg, 43%).

Step 6 To a stirred solution of compound 0 (1.0 eq) and 1,3-dimethyl-5-(4,4,5,5-tetramethyl-[1,3,2]dioxaborolan-2-yl)-1H-indazole (1.3 eq) in dioxane:water (14 mL, 20 V) were added potassium carbonate (2.5 eq) and $PdCl_2(dppf)$ DCM (0.1 eq) at RT. The resulting reaction mass was stirred at 90° C. for 6 hours. The reaction was monitored by TLC. The reaction mass was diluted with ethyl acetate (200 mL) and filtered through celite pad. The organic layer was washed with water (100 mL), brine (50 mL), dried over anhydrous sodium sulphate and concentrated. The crude product was purified by silica gel (230-400) column chromatography (6% methanol in dichloromethane) to obtain a compound of formula (Ig).

The compounds of Examples 20 to 28 were synthesized by following the General Procedure 3, using the appropriate amines of formula (III). The analytical data are shown in Table 4.

TABLE 4

| Ex. | Analytical Data |
|---|---|
| 20 | $^1$H-NMR (DMSO, 400 MHz): δ 9.28 (s, 1H), 8.52 (d, 2H), 7.84 (s, 1H), 7.71 (d, 1H), 7.61 (d, 1H), 7.36 (d, 2H), 4.74 (d, 2H), 3.98 (s, 3H), 2.55 (s, 3H), 2.50 (s, 3H), 2.35 (s, 3H), LCMS: 399.3 [M + H], HPLC purity: 98.48% |
| 21 | $^1$H-NMR (DMSO, 400 MHz): δ 9.14 (s, 1H), 8.41 (s, 1H), 7.82 (s, 1H), 7.70 (d, 1H), 7.60 (d, 1H), 7.32 (d, 2H), 6.90 (d, 2H), 4.63 (d, 2H), 3.97 (s, 3H), 3.97 (s, 3H), 3.71 (s, 3H), 2.54 (s, 3H), 2.50 (s, 3H), 2.35 (s, 3H), LCMS: 428.3 [M + H], HPLC purity: 97.12% |
| 22 | $^1$H-NMR (DMSO, 400 MHz): δ 9.26 (s, 1H), 8.49 (d, 1H), 7.82 (d, 1H), 7.58 (m, 2H), 7.60 (d, 1H), 7.20 (d, 2H), 4.67 (d, 2H), 3.97 (s, 3H), 2.53 (s, 3H), 2.50 (s, 3H), 2.40 (s, 3H), 2.35 (s, 3H), LCMS: 413.3 [M + H], HPLC purity: 93.78% |
| 23 | $^1$H-NMR (DMSO, 400 MHz): δ 9.32 (s, 1H), 7.84 (s, 1H), 7.78 (d, 2H), 7.71 (d, 1H), 7.68 (d, 1H), 7.60 (d, 2H), 7.33 (s, 2H), 4.78 (d, 2H), 3.98 (s, 3H), 2.54 (s, 3H), 2.50 (s, 3H), 2.35 (s, 3H), LCMS: 477.4 [M + H], HPLC purity: 99.97% |
| 24 | $^1$H-NMR (DMSO, 400 MHz): δ 9.26 (t, 1H) 7.83 (s, 1H), 7.69 (d, 1H), 7.61 (d, 1H), 7.40 (m, 4H), 4.70 (d, 2H), 3.98 (s, 3H), 3.08 (s, 3H), 2.60 (s, 3H), 2.53 (s, 3H), 2.50 (s, 3H), 2.37 (s, 3H), LCMS: 432.7 [M + H], HPLC purity: 99.84% |
| 25 | $^1$H-NMR (DMSO, 400 MHz): δ 9.34 (t, 1H) 8.02 (s, 1H), 7.84 (d, 2H), 7.75 (d, 1H), 7.69 (d, 4H), 7.62 (m, 2H), 4.81 (d, 2H), 3.98 (s, 3H), 3.18 (s, 3H), 2.54 (s, 3H), 2.50 (s, 3H), 2.38 (s, 3H), LCMS: 476.6 [M + H], HPLC purity: 94.13% |
| 26 | $^1$H-NMR (DMSO, 400 MHz): δ 9.68 (bs, 1H) 9.18 (s, 1H), 7.83 (s, 1H), 7.69 (d, 1H), 7.60 (d, 1H), 7.37 (d, 2H), 7.17 (d, 2H), 4.67 (d, 2H), 3.98 (s, 3H), 2.96 (s, 3H), 2.54 (s, 3H), 2.50 (s, 3H), 2.38 (s, 3H), LCMS: 491.9 [M + H], HPLC purity: 99.91% |
| 27 | $^1$H-NMR (CDCl$_3$, 400 MHz): δ 7.81 (s, 1H), 7.68 (d, 1H), 7.40 (d, 1H), 7.21 (d, 1H), 7.12 (d, 1H), 7.00 (d, 1H), 6.75 (d, 1H), 5.03 (d, 2H), 4.03 (s, 3H), 2.60 (s, 3H), 2.58 (s, 3H), 2.54 (s, 3H), LCMS: 404.4 [M + H], HPLC purity: 99.32% |
| 28 | $^1$H-NMR (DMSO, 400 MHz): δ 9.19 (s, 1H), 8.18 (t, 1H), 7.82 (s, 1H), 7.78 (d, 1H), 7.69 (d, 1H), 7.60 (d, 1H), 6.79 (d, 1H), 4.63 (d, 2H), 3.97 (s, 3H), 3.81 (s, 3H), 2.52 (s, 3H), 2.50 (s, 3H), 2.41 (s, 3H), LCMS: 429.6 [M + H], HPLC purity: 99.61% |

Amines $R_4NH_2$ of use to prepare compounds of the invention are commercially available or may be easily synthesized by the person of ordinary skill in the art. The amines used in each one of the Examples 1-28 are indicated in Table 5.

TABLE 5

| Examples | $R_4NH_2$ |
|---|---|
| 1, 8, 20 | pyridin-4-ylmethanamine |
| 2, 9, 22 | (6-methylpyridin-3-yl)methanamine |
| 3, 11, 24 | (4-chlorophenyl)methanamine |
| 4, 14, 28 | (6-methoxypyridin-3-yl)methanamine |
| 5, 15, 27 | thiophen-2-ylmethanamine |
| 6, 10, 21 | (4-methoxyphenyl)methanamine |
| 7, 12, 25 | (3-(methylsulfonyl)phenyl)methanamine |
| 13, 23 | 4-(aminomethyl)benzenesulfonamide |
| 16, 26 | N-(4-(aminomethyl)phenyl)methanesulfonamide |
| 17 | (6-trifluoromethylpyridin-3-yl)methanamine |
| 18 | benzylamine |
| 19 | (4-fluorophenyl)methanamine |

Compounds of the general formula (Ih) as defined herein above may be prepared e.g. by following the teachings in Maechling S., et al, J. Comb. Chem. 2010, 12, 818-821.

Biological Assays

In Vitro Assay in Mammalian Cell Culture

The antiviral activity of the compounds of the invention has been evaluated based on the ability of the compounds to prevent virus from causing viral cytopathic effects (CPE) in mammalian cell culture. Incubation time, cell line, cell density and virus titer differed from assay to assay but the general procedure was as follows:

Cells were cultivated on 96-well flat bottom plates to approximately 90% confluence (20 000-90 000 cells/well) in a suitable media. The titer of the virus was determined by the standard method of tissue culture infective dose ($TCID_{50}$) on cells. Briefly, cells were infected with 50 µl of virus suspension, and diluted 10-fold in media. The plates were incubated in 37° C. with 5% $CO_2$ for 3-7 days and cells were inspected daily for CPE. After determining CPE, plates were stained with Gram's Crystal Violet solution and optical density was read at 540 nm. The highest virus dilution that resulted in >95 CPE was used in the assays. Substances at a final concentration of 0.1 nM-1 µM and the virus were added to the cells and incubated for 3-7 days depending on the virus and cell line used. As controls, uninfected cells and cells infected with virus (no substance) were included on each plate. The cells were stained with crystal violet after determining the CPE on infected controls and the optical density was read at 540 nm. The inhibition capacity was calculated as a % by comparison with non-infected and infected controls.

The dose response of inhibition of Coxsackie B3 Nancy strain induced cytopathogenic effect was measured using 6 different compounds of the present invention, viz. Examples 2, 3, 8, 20 and 25. The test was run at 1 (High) and 0.1 (Low) multiplicity of infection (MOI). The results are shown in FIG. 1.

Table 6 shows the inhibition capacity of compounds of the invention on different enteroviruses. EV6: Enterovirus 6; EV30: Enterovirus 30; EV68: Enterovirus 68; EV71: Enterovirus 71; B1: coxsackie B1 virus; B2: coxsackie B2 virus; B3: coxsackie B3 virus; B4: coxsackie B4 virus; B5: coxsackie B5 virus; Polio1: polio virus Sabin 1.

TABLE 6

| Ex. | EV6 | EV30 | EV68 | EV71 | B1 | B2 | B3 | B4 | B5 | Polio 1 |
|---|---|---|---|---|---|---|---|---|---|---|
| 1 | +++ | 5+ | ++ | +++ | +++ | +++ | 4+ | nd | 5+ | 4+ |
| 2 | ++ | ++ | + | ++ | ++ | ++ | +++ | +++ | ++ | ++ |
| 3 | + | + | + | + | ++ | + | + | + | nd | + |
| 4 | + | ++ | + | ++ | ++ | ++ | ++ | ++ | nd | + |
| 5 | ++ | ++ | + | ++ | 4+ | ++ | ++ | ++ | nd | ++ |
| 6 | nd | + | + | nd | + | + | + | + | + | + |
| 7 | nd | ++ | 4+ | 4+ | +++ | +++ | 4+ | ++ | +++ | +++ |
| 8 | ++ | 4+ | 5+ | 5+ | 5+ | 5+ | 5+ | +++ | 5+ | 5+ |
| 9 | + | ++ | ++ | ++ | +++ | +++ | +++ | ++ | ++ | ++ |
| 10 | + | ++ | + | + | + | + | ++ | ++ | ++ | + |
| 11 | + | + | + | + | + | + | + | ++ | + | + |
| 12 | +++ | 4+ | ++ | +++ | +++ | +++ | 4+ | 4+ | 4+ | +++ |
| 13 | + | ++ | + | ++ | + | + | ++ | ++ | ++ | ++ |
| 14 | + | ++ | + | + | + | + | +++ | +++ | + | ++ |
| 15 | ++ | ++ | ++ | ++ | ++ | ++ | ++ | ++ | ++ | ++ |
| 16 | + | + | + | + | + | + | ++ | ++ | + | + |
| 17 | + | + | nd | ++ | nd | + | + | + | + | + |
| 18 | + | nd | nd | +++ | nd | ++ | ++ | + | + | ++ |
| 19 | + | nd | nd | ++ | nd | + | ++ | + | + | + |
| 20 | + | +++ | +++ | +++ | 4+ | 4+ | 4+ | +++ | 4+ | 4+ |
| 21 | nd | + | + | ++ | + | + | ++ | + | + | +++ |
| 22 | + | ++ | ++ | +++ | +++ | +++ | 4+ | + | ++ | 4+ |
| 23 | ++ | ++ | ++ | +++ | ++ | ++ | ++ | +++ | ++ | ++ |
| 24 | + | ++ | + | ++ | ++ | ++ | ++ | ++ | + | ++ |
| 25 | +++ | +++ | +++ | +++ | +++ | +++ | +++ | 4+ | +++ | 4+ |
| 26 | + | ++ | ++ | ++ | +++ | ++ | ++ | ++ | nd | + |
| 27 | ++ | ++ | ++ | ++ | 4+ | 4+ | +++ | 4+ | nd | ++ |
| 28 | + | ++ | + | ++ | +++ | ++ | ++ | ++ | nd | + |

In Table 6 the signs have the following meaning:

| + | $IC_{50} < 1$ µM |
|---|---|
| ++ | $IC_{50} < 100$ nM |
| +++ | $IC_{50} < 10$ nM |
| 4+ | $IC_{50} < 1$ nM |
| 5+ | $IC_{50} < 0.1$ nM |

Time of addition assay The assay was performed like the "in vitro assay in mammalian cell culture" described above with the exception that substance was added one hour pre inoculation (−1 h), at inoculation (0 h), and 2 hours (+2 h), 6 hours (+6 h) or 24 hours (+24 h) past inoculation. The virus EV71 was used at high titer for the test. Table 7 shows data for Example 7 and Example 20. The data show that the time of addition of the drug was not crucial and as long the replication was not too quick the compound could inhibit the cytopathogenic effect in an efficient way.

TABLE 7

| Ex. | Conc. | −1 h | 0 h | +2 h | +6 h | +24 h |
|---|---|---|---|---|---|---|
| 7 | 100 nM | 0.95 | 0.85 | 1.00 | 0.91 | 0.02 |
| 20 | 100 nM | 0.85 | 0.94 | 0.95 | 0.99 | 0.02 |

Phosphatidyl inositol kinase inhibition assay Inhibition of PI4 kinases was studied using the ADP-Glo™ Kinase Assay which is a luminescent kinase assay that measures ADP formed from a kinase reaction, wherein ADP is converted into ATP, which is converted into light by Ultra-Glo™ Luciferase. The assay is performed in two steps; first, after the kinase reaction, an equal volume of ADP-Glo™ Reagent is added to terminate the kinase reaction and deplete the remaining ATP. In the second step, the Kinase Detection Reagent is added, which simultaneously converts ADP to ATP and allows the newly synthesized ATP to be measured using a coupled luciferase/luciferin reaction. The luminescent signal produced is proportional to the activity of the kinase. Inhibition of PI3 kinases was studied using the HTRF (homogeneous time-resolved fluorescence) assay, which is a universal method for identifying and characterizing the phosphotransferase activity induced by any ATP/ADP dependent target. The formation of ADP was detected by a specific monoclonal antibody labeled with $Eu^{3+}$ cryptate, and directly correlated with the amount of phosphorylated substrate. Table 8 shows test results for some compounds of the invention vs. different kinases, expressed as $IC_{50}$ values (in µM).

TABLE 8

| Kinase | Example 2 $IC_{50}$ (µM) | Example 8 $IC_{50}$ (µM) | Example 12 $IC_{50}$ (µM) | Example 20 $IC_{50}$ (µM) |
|---|---|---|---|---|
| PI4KIIIβ | 0.0015 | 0.0009 | 0.0008 | 0.0012 |
| PI4KIIIα | 0.2 | 1.3 | 0.8 | >1* |
| PI3Kβ | 1.7 | 1.5 | >1* | >1* |
| PI3Kα | >1* | >1* | >1* | >1* |

*No inhibition at the highest texted concentration 1 µM

Pharmacokinetics in Male Sprague Dawley Rats

Figure 2:
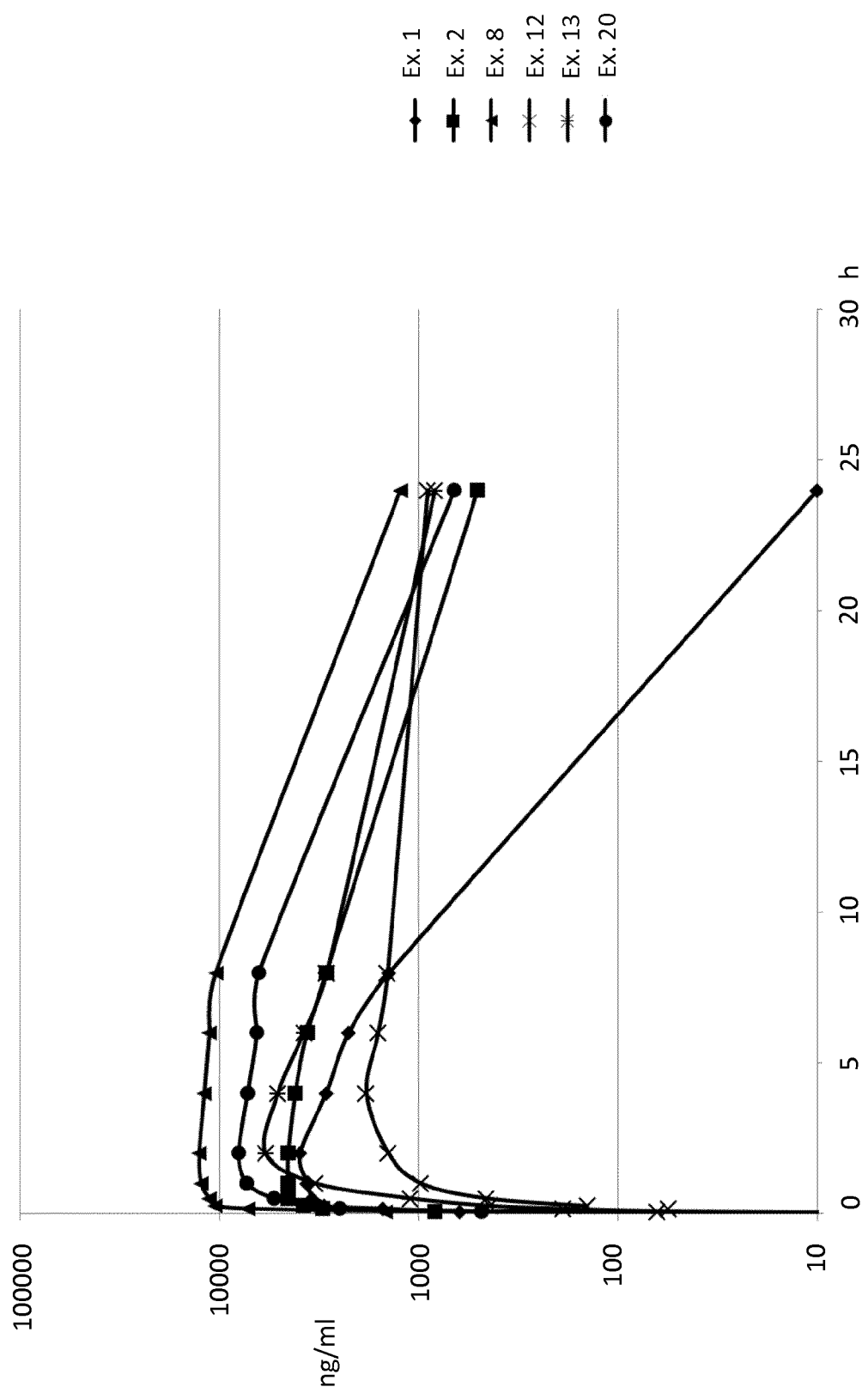
FIG. 2 is a graph showing the pharmacokinetic profile, expressed as ng/ml of compound of the invention in samples of blood extracted from rats at different time points after administration of 6 different compounds of the present invention at a dose of 50 mg/kg.

Overnight fasted animals were administered with the test compounds in recommended vehicle 0.4% (v/v) Tween 80+2% (v/v) Glycerol and 15% w/v HPBCD by oral route with a dose of 50 mg/kg body weight at dose volume of 10 mL/kg bw. Under mild isoflurane anesthesia, blood samples were collected into pre-labeled tubes containing anticoagulant ($K_2$EDTA—2 mg/mL blood) during the next 24 hours post dose. Collected blood samples were centrifuged at 4000 rpm, 4° C. for 10 minutes and plasma was separated and stored at −80° C. until analysis. The analysis showed that the compounds of the invention are orally available with good to excellent bioavailability. Test data are shown in Table 9 and in FIG. 2.

TABLE 9

| Parameter | Ex. 1 | Ex. 2 | Ex. 8 | Ex. 12 | Ex. 13 | Ex. 20 |
|---|---|---|---|---|---|---|
| Dose (mg/kg bw) | 50.00 | 50.00 | 50.00 | 50.00 | 50.00 | 50.00 |
| $C_{max}$ (µg/mL) | 3.9 ± 0.4 | 4.8 ± 0.8 | 12.9 ± 0.7 | 1.9 ± 0.1 | 5.9 ± 0.9 | 8.0 ± 1.5 |
| $T_{max}$ (h) | 1.7 ± 0.6 | 1.7 ± 0.6 | 1.7 ± 0.6 | 5.3 ± 2.3 | 2 ± 0 | 2 ± 0 |
| $AUC_{last}$ (h * µg/mL) | 22.2 ± 2.1 | 58.6 ± 9.9 | 184.7 ± 13.3 | 30.0 ± 8.2 | 62.1 ± 10.9 | 109.8 ± 8.3 |
| $AUC_{inf}$ (h * µg/mL) | 31.8 ± 8.0 | 64.1 ± 7.0 | 196.9 ± 27.1 | 73.3 ± 46.9 | 76.1 ± 26.8 | 115.0 ± 9.4 |
| $AUC_{extrap}$ (%) | 27.8 ± 14.8 | 8.8 ± 7.1 | 5.7 ± 6.1 | 49.4 ± 24.5 | 14.5 ± 17.1 | 5.1 ± 4.9 |
| $T_{1/2}$ (h) | 4.3 ± 2.0 | 6.6 ± 2.4 | 5.4 ± 2.5 | 27.6 ± 16.8 | 8.2 ± 5.4 | 5.0 ± 2.3 |
| $MRT_{last}$ (h) | 3.4 ± 0.2 | 6.9 ± 0.8 | 6.8 ± 0.8 | 10.3 ± 1.2 | 7.5 ± 1.4 | 6.8 ± 0.9 |

Metabolic stability in human and rat liver microsomes- Metabolic stability was studied using human (HLM) or rat (RLM) liver microsomes. The final composition of the assay included 5 µM of test item and reference item (Diclofenac or Imipramine) prepared from DMSO stock, so that the final concentration of DMSO was 0.1%, 0.125 mg/mL microsomal protein and cofactors (5.0 mM G-6-P, 0.06 U/mL G-6-PDH, 2.0 mM $MgCl_2$, 1.0 mM $NADP^+$). Test and reference items were incubated with human or rat liver microsomes with or without cofactors. The reaction mixture (100 µL) was removed at specified time periods and the reaction was stopped by addition of stop solution. The samples were extracted in presence of internal standard and were analyzed using LC-MS/MS. The percent of the test/ reference item remaining after a specified incubation period was calculated with respect to the peak area ratio at time 0 min. Results are shown in Table 10.

Human and Rat Plasma Protein Binding by Rapid Equilibrium Dialysis Method

Plasma protein binding study was performed by using a Rapid Equilibrium Dialysis (RED) device containing dialysis membrane with a molecular weight cut-off of 8,000 Daltons. Each dialysis insert contains two chambers. The red chamber was for the plasma while the white chamber was for the buffer. The human and rat plasma (pH adjusted to 7.40) samples of test items and reference items (Warfarin and Propranolol) were prepared at a required test concentration of 5 µM using 5 mM DMSO stocks (final DMSO concentration was 0.1%). 300 µL of plasma sample was added into the sample chamber. 500 µL of buffer was added into the buffer chamber. After sealing the RED device with an adhesive film, incubation was done at 37° C. with shaking at 300 rpm for 4 h. Following incubation, an aliquot of 50 µL was removed from each well (plasma and buffer side) and diluted with equal volume of opposite matrix to nullify the matrix effect. The specimens were subjected to sample extraction in presence of internal standard by liquid-liquid extraction/protein precipitation method. After extraction, the samples were transferred into labeled auto sampler vials and submitted to LC-MS/MS analysis. Results are shown in Table 10.

TABLE 10

| Ex. | Remaining after 1 h, HLM | Remaining after 1 h, RLM | t½ HLM with cofactors | Plasma protein binding, human | Plasma protein binding, rat |
|---|---|---|---|---|---|
| 1 | 90% | 88% | >120 min | 98.4% | 97.0% |
| 7 | 75% | 94% | >120 min | 99.5% | 99.4% |
| 8 | 86% | 90% | >120 min | 97.3% | 97.6% |
| 12 | 84% | 71% | >120 min | 99.0% | 98.5% |
| 20 | 78% | 96% | >120 min | 9.4% | 96.9% |

7 Days Toxicity Studies in Rats

Based on previous toxicity tests with analogs and pharmacokinetic data, repeated dose toxicity and toxicokinetic studies were conducted to generate information on the toxic characteristics of some representative compounds of the invention, viz. Example 8 and Example 12, respectively, when administered orally by gavage to Sprague Dawley rats for a period of 7 consecutive days. The study plan for the studies was by current ICH guidelines for 7 days toxicity studies and the No Observed Adverse Effect Level (NOAEL) of Example 8 and Example 12 was determined as 60 mg/kg body weight/day and 50 mg/kg bodyweight/day respectively when administered once daily orally to Sprague Dawley rats for 7 consecutive days under the tested dose levels and experimental conditions employed.

CVB3-Induced Pancreatitis Mouse Model

Figure 3:
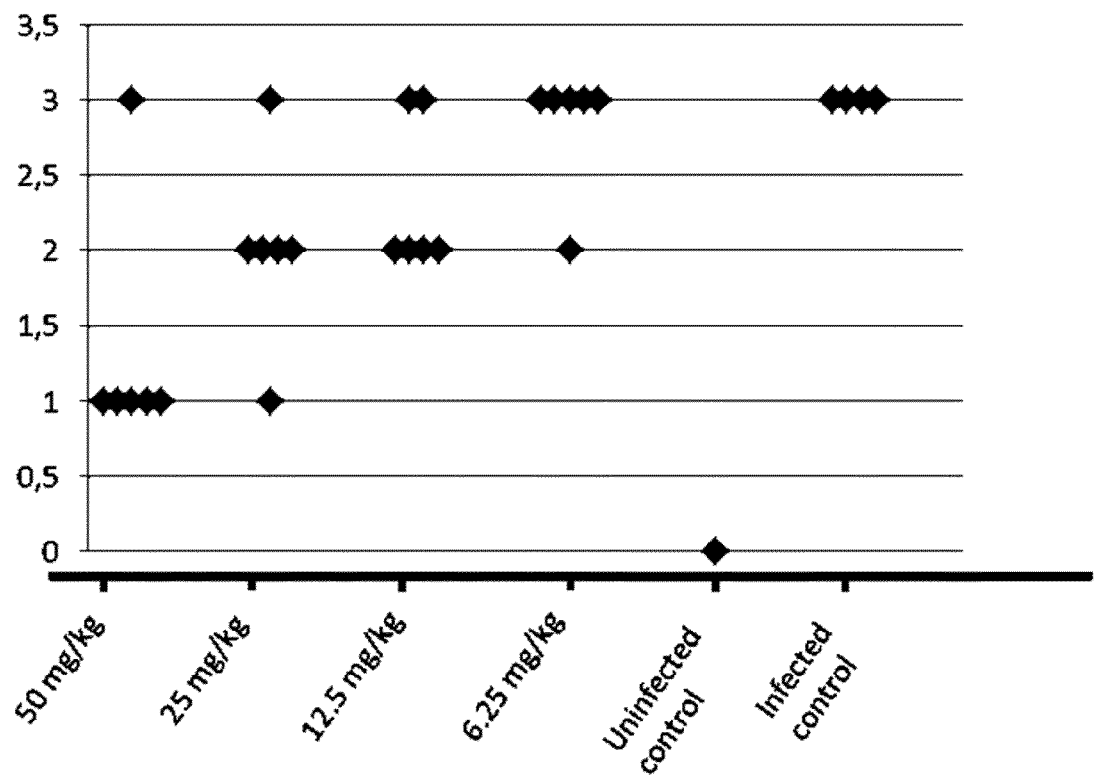
FIG. 3 is a graph showing pancreatitis scoring in Coxsackie B3, Nancy strain infected SJL mice after treatment with different doses of Example 8. 0=no abnormalities. 1=slight inflammation and/or single cell foci in exocrine pancreas. 2=moderate inflammation and/or several foci with necrosis in exocrine pancreas. 3=severe inflammation and/or large areas of necrosis in exocrine pancreas.
Figure 4:
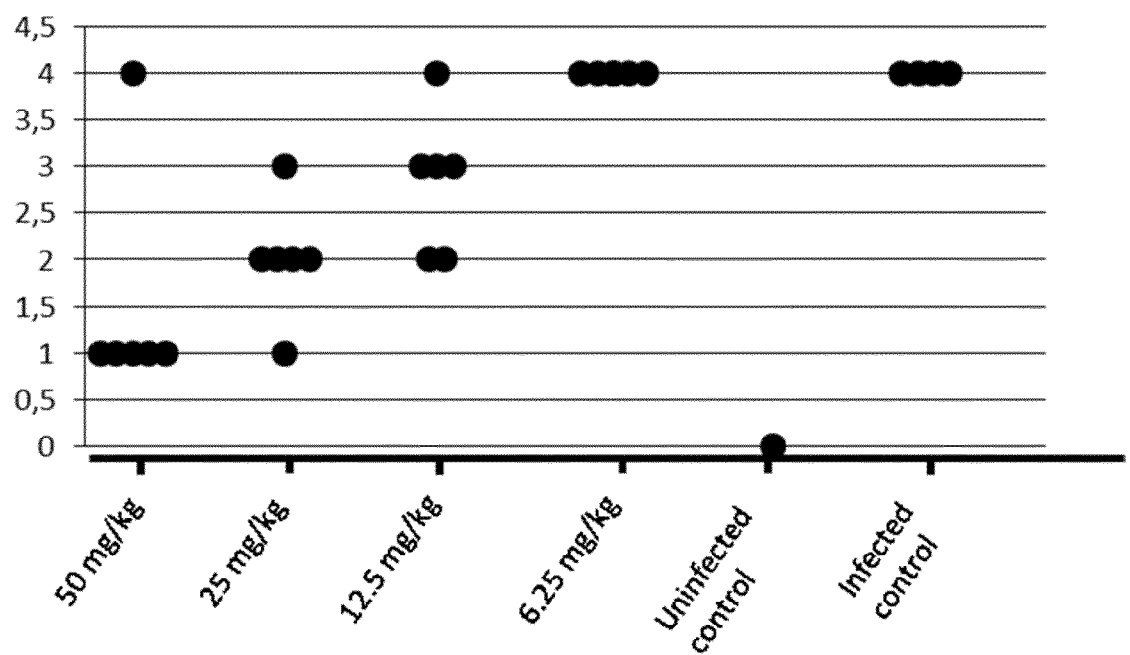
FIG. 4 is a graph showing the virus titer scoring in Coxsackie B3, Nancy strain infected SJL mice after treatment with different doses of Example 8, based on immunohistochemistry using the Dako 5-D8/1 monoclonal mouse antibody. A score 4 indicates the highest virus titer and a score 0 indicates no infection
Figure 5:
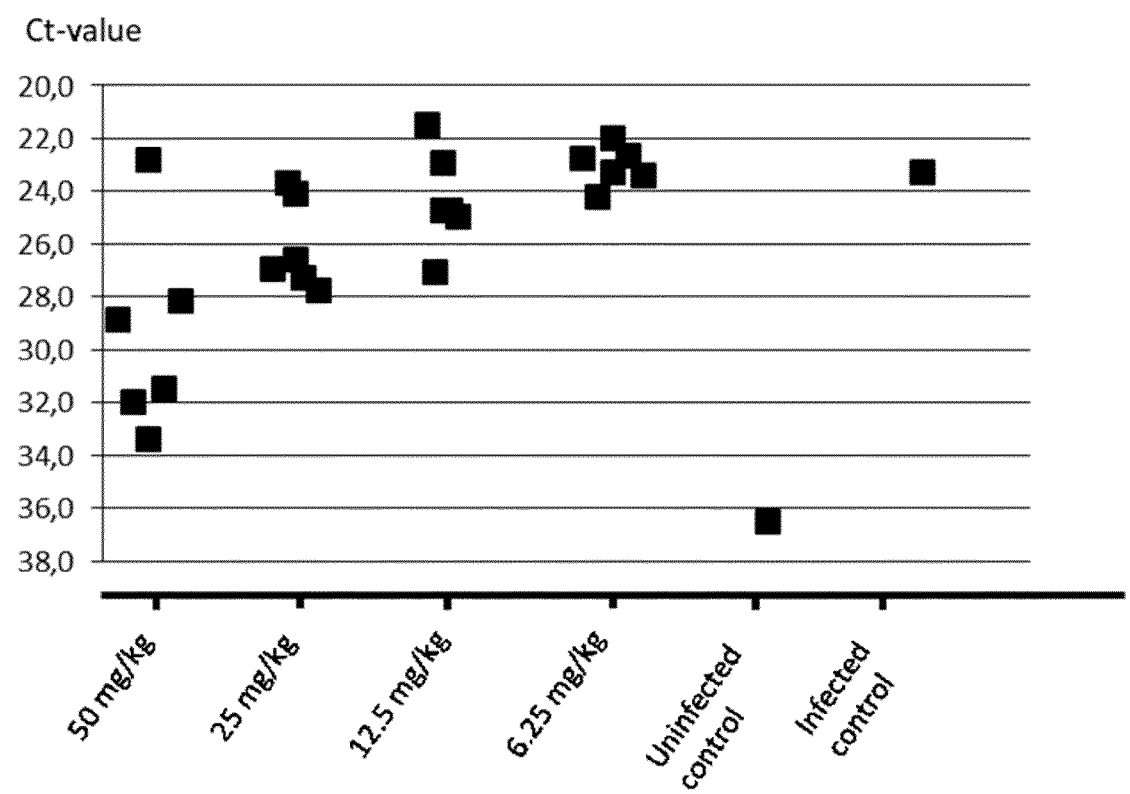
FIG. 5 is a graph showing the Ct values from PCR detection of virus titer in Coxsackie B3, Nancy strain infected SJL mice after treatment with different doses of Example 8.
Figure 6:
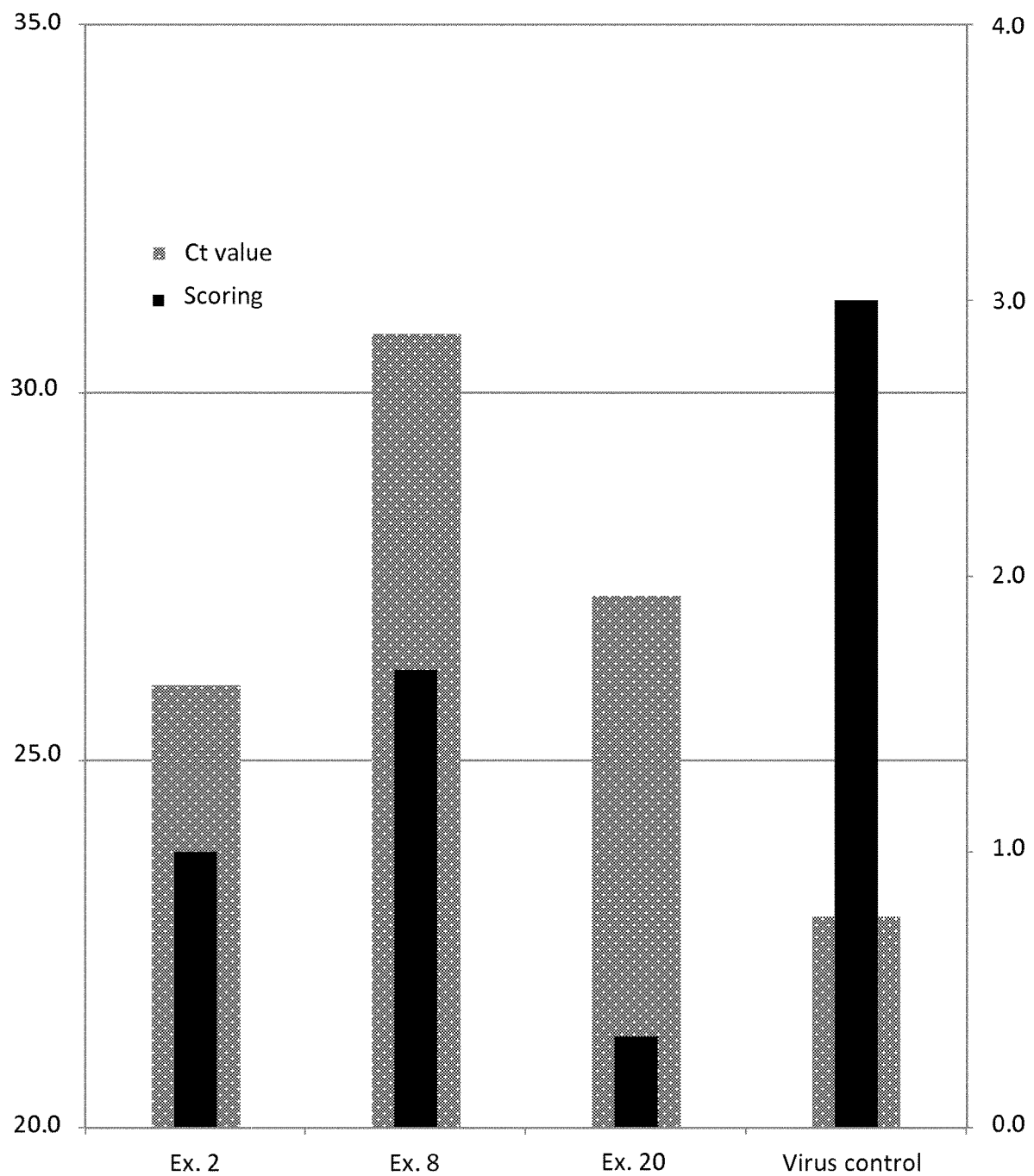
FIG. 6 is a bar chart showing the results from average pancreatitis scoring as well as average Ct values from PCR detection of virus titer, in Coxsackie B3, Nancy strain infected SJL mice after treatment with at a fixed dose of 50 mg/kg/day for Example 2, 8 and 20, respectively. Coxsackie B3, Nancy strain infected SJL mice receiving no treatment were used as controls.

Compounds of the present invention were studied in a CVB3 induced pancreatitis mouse model as described by van der Schaar et al (Antimicrob. Agents Chemother. 2013, 57(10):4971-4981). Animals (SJL mice) were infected intraperitoneally with 0.3 ml Coxsackie B3 (Nancy strain) virus (log $TCID_{50}$=8). The animals were treated 2 h pre-infection and then once daily for 3 days. The animals were euthanized and organs were collected for pancreatitis evaluation by histopathology and for virus titer determination by immunohistochemistry and polymerase chain reaction (PCR). Pancreata were obtained from infected and uninfected control animals and from animals treated with 4 different dosages of Example 8, and HE-stained slides of the organs were prepared, studied and scored for signs of inflammation and necrosis on a scale from 0 to 3, as follows: 0=no abnormalities. 1=slight inflammation and/or single cell foci in exocrine pancreas. 2=moderate inflammation and/or several foci with necrosis in exocrine pancreas. 3=severe inflammation and/or large areas of necrosis in exocrine pancreas (FIG. 3). The virus titer in the organs was determined by immunohistochemistry using the Dako 5-D8/1 monoclonal mouse antibody and the titer was scored on a scale from 0 to 4, where 0 indicates no infection and 4 corresponds to the highest determined virus titer (FIG. 4). The Ct values from PCR detection of virus titers were determined (FIG. 5). The higher the Ct value is, the lower is the virus titer. The data show a very good dose-response. Corresponding studies were also performed on Examples 2, 8 and 20 at a dosage of 50 mg/kg/day and pancreatitis scoring and Ct values were determined (FIG. 6).

The invention claimed is:

1. A compound of formula (I):

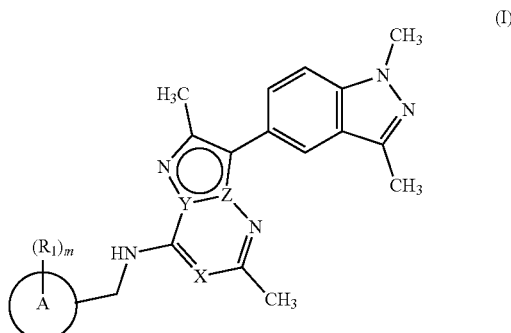

or a pharmaceutically acceptable salt thereof, wherein:

m is 0, 1, or 2;

ring A is phenyl, 5-membered heteroaryl, or 6-membered heteroaryl, wherein the heteroaryl has one or more heteroatoms independently selected from the group consisting of nitrogen, oxygen, and sulfur;

each $R_1$ is independently halogen, $C_1$-$C_6$ alkyl, $C(O)R_{10}$, $C(O)NR_6R_7$, $NR_{11}R_{12}$, $NR_9C(O)R_8$, $NR_5S(O)_2R_4$, $OR_2$, $S(O)_2R_3$, or $S(O)_2NR_{13}R_{14}$, wherein the $C_1$-$C_6$ alkyl is optionally substituted by one or more independently selected halogen atoms;

each $R_2$ is independently H or $C_1$-$C_6$ alkyl, wherein the $C_1$-$C_6$ alkyl is optionally substituted by one or more independently selected halogen atoms;

each $R_3$ is independently H or $C_1$-$C_6$ alkyl, wherein the $C_1$-$C_6$ alkyl is optionally substituted by one or more independently selected halogen atoms;

each $R_4$ is independently H or $C_1$-$C_6$ alkyl, wherein the $C_1$-$C_6$ alkyl is optionally substituted by one or more independently selected halogen atoms;

each $R_5$ is independently H or $C_1$-$C_6$ alkyl, wherein the $C_1$-$C_6$ alkyl is optionally substituted by one or more independently selected halogen atoms;

each $R_6$ is independently H or $C_1$-$C_6$ alkyl, wherein the $C_1$-$C_6$ alkyl is optionally substituted by one or more independently selected halogen atoms;

each $R_7$ is independently H or $C_1$-$C_6$ alkyl, wherein the $C_1$-$C_6$ alkyl is optionally substituted by one or more independently selected halogen atoms;

each $R_8$ is independently H or $C_1$-$C_6$ alkyl, wherein the $C_1$-$C_6$ alkyl is optionally substituted by one or more independently selected halogen atoms;

each $R_9$ is independently H or $C_1$-$C_6$ alkyl, wherein the $C_1$-$C_6$ alkyl is optionally substituted by one or more independently selected halogen atoms;

each $R_{10}$ is independently H or $C_1$-$C_6$ alkyl, wherein the $C_1$-$C_6$ alkyl is optionally substituted by one or more independently selected halogen atoms;

each $R_{11}$ is independently H or $C_1$-$C_6$ alkyl, wherein the $C_1$-$C_6$ alkyl is optionally substituted by one or more independently selected halogen atoms;

each $R_{12}$ is independently H or $C_1$-$C_6$ alkyl, wherein the $C_1$-$C_6$ alkyl is optionally substituted by one or more independently selected halogen atoms;

each $R_{13}$ is independently H or $C_1$-$C_6$ alkyl, wherein the $C_1$-$C_6$ alkyl is optionally substituted by one or more independently selected halogen atoms;

each $R_{14}$ is independently H, $C_1$-$C_6$ alkyl, $C(O)R_{15}$, or $C(O)OR_{16}$, wherein the $C_1$-$C_6$ alkyl is optionally substituted by one or more independently selected halogen atoms;

each $R_{15}$ is independently H or $C_1$-$C_6$ alkyl, wherein the $C_1$-$C_6$ alkyl is optionally substituted by one or more independently selected halogen atoms;

each $R_{16}$ is independently H or $C_1$-$C_6$ alkyl, wherein the $C_1$-$C_6$ alkyl is optionally substituted by one or more independently selected halogen atoms;

X is CH or N; and (i) Y is N; and
Z is C; or
(ii) Y is C; and
Z is N.

2. The compound of claim 1, or a pharmaceutically acceptable salt thereof, wherein ring A is phenyl or 6-membered heteroaryl.

3. The compound of claim 2, or a pharmaceutically acceptable salt thereof, wherein:

is formula (IIa):

wherein:
$W_1$ is CH, $CR_1$, or N; and
$W_2$ is CH, $CR_1$, or N.

4. The compound of claim 3, or a pharmaceutically acceptable salt thereof, wherein:

5. The compound of claim 4, or a pharmaceutically acceptable salt thereof, wherein:

6. The compound of claim 1, or a pharmaceutically acceptable salt thereof, wherein ring A is 5-membered heteroaryl or 6-membered heteroaryl.

7. The compound of claim 1, or a pharmaceutically acceptable salt thereof, wherein X is CH.

8. The compound of claim 1, or a pharmaceutically acceptable salt thereof, wherein X is N.

9. The compound of claim 1, or a pharmaceutically acceptable salt thereof, wherein:

Y is N; and

Z is C.

10. The compound of claim 1, or a pharmaceutically acceptable salt thereof, wherein:

Y is C; and

Z is N.

11. The compound of claim 1, wherein the compound is selected from the group consisting of:

51
-continued
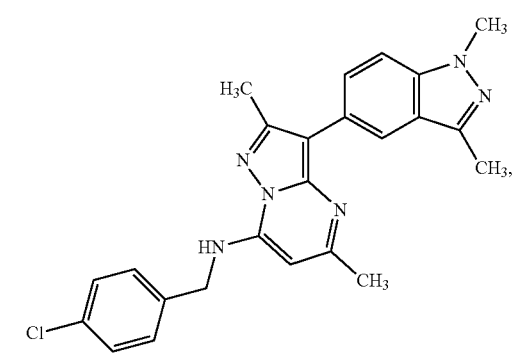
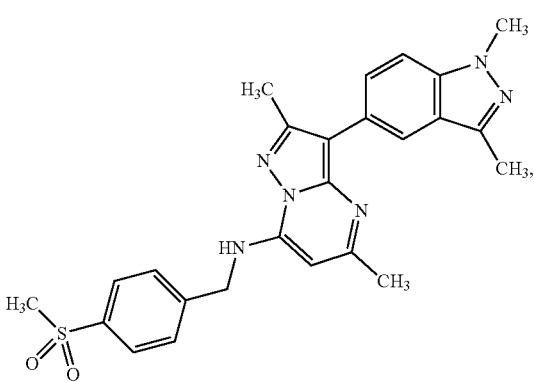
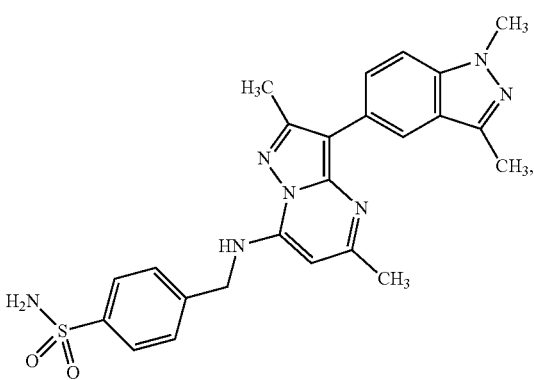
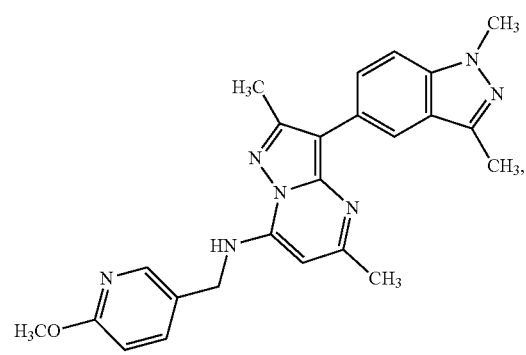
52
-continued
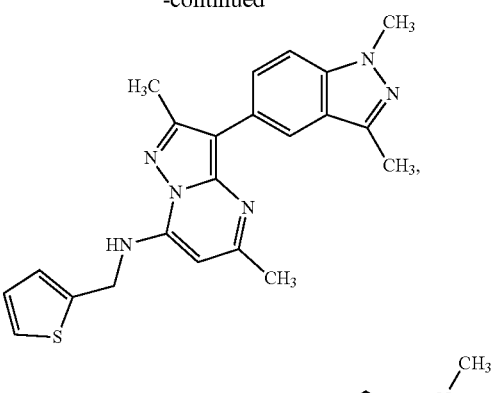
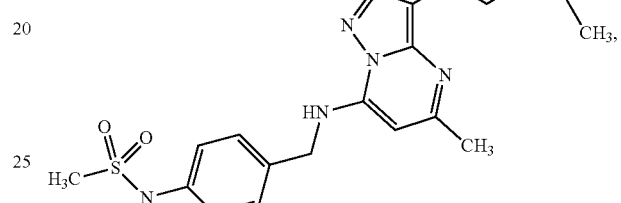
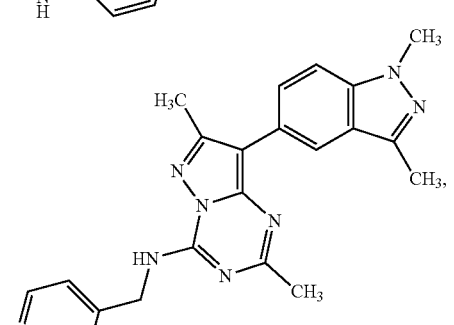
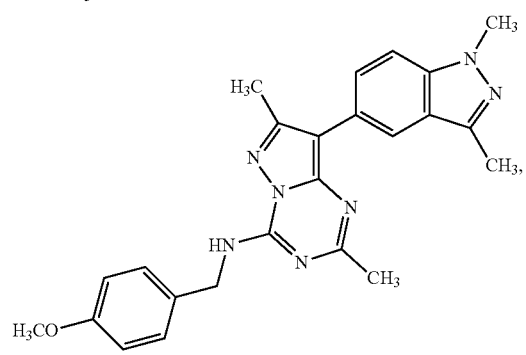
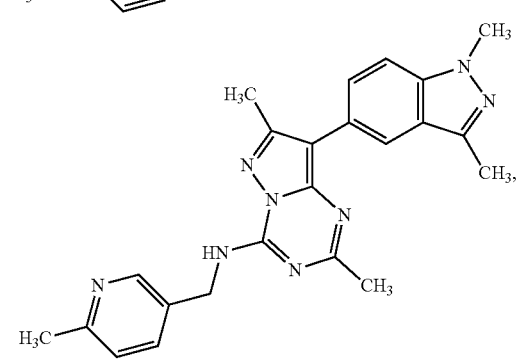

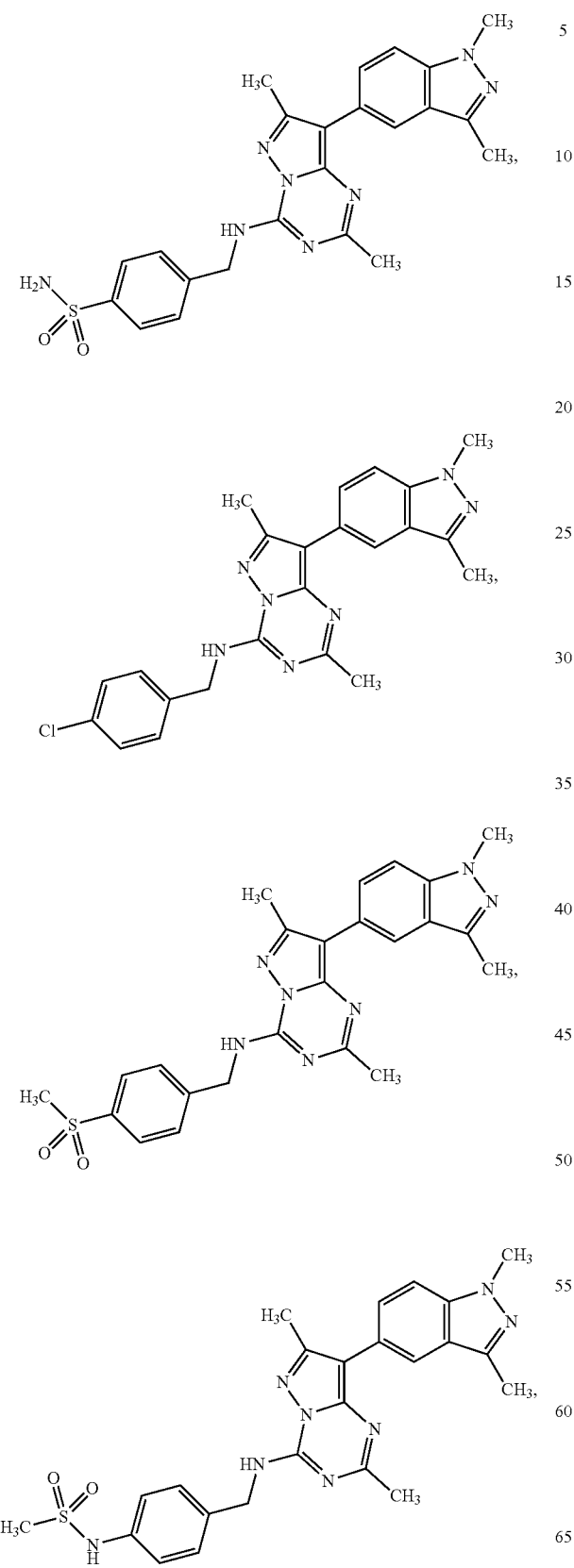
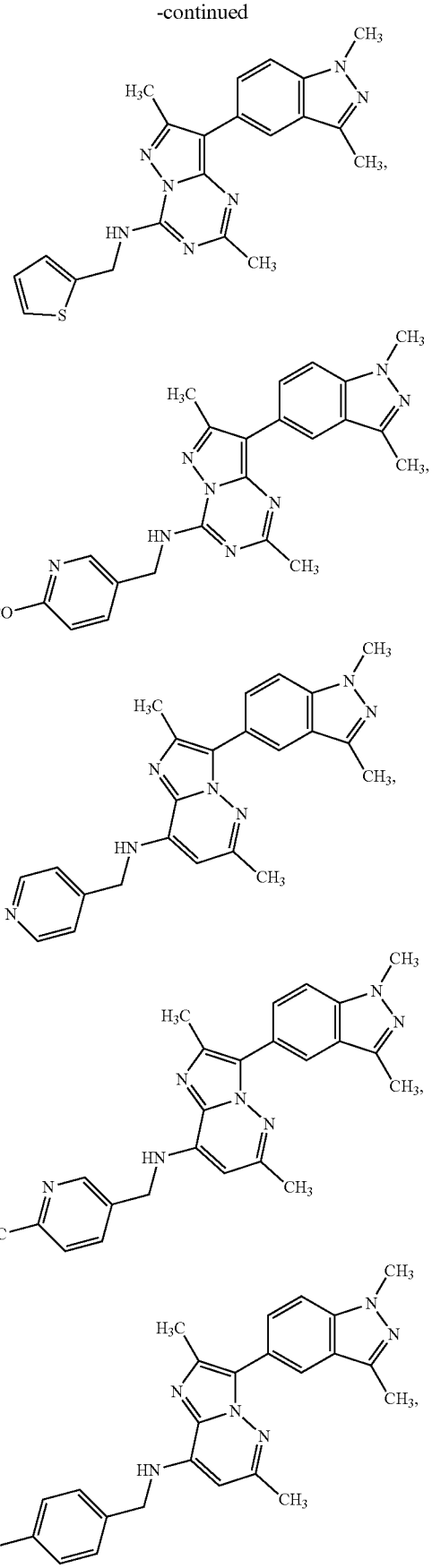

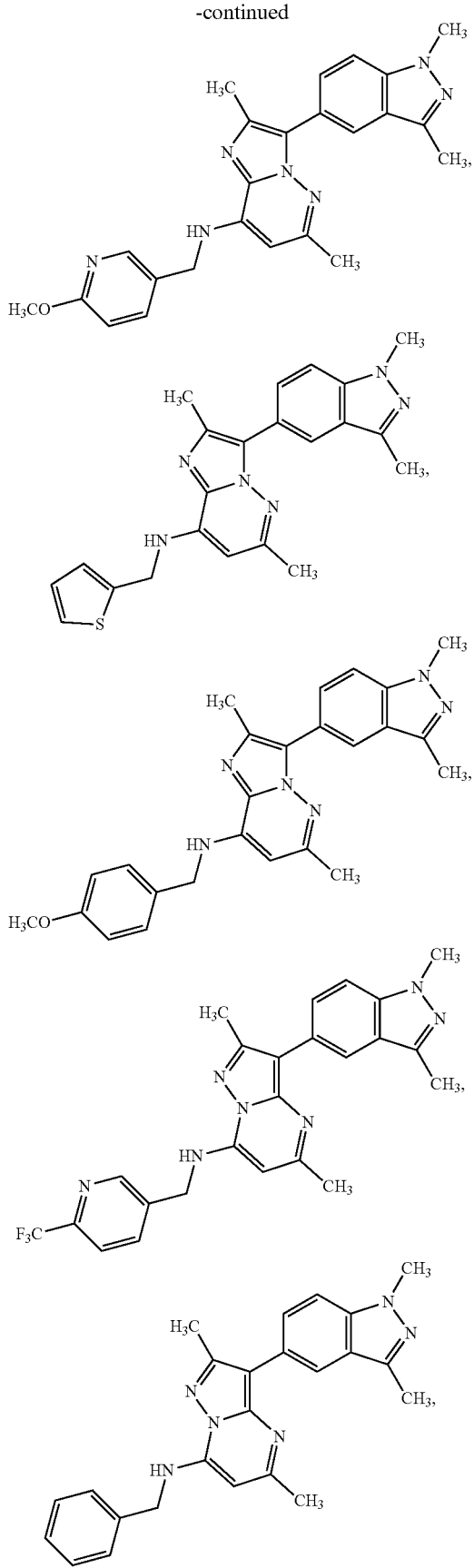

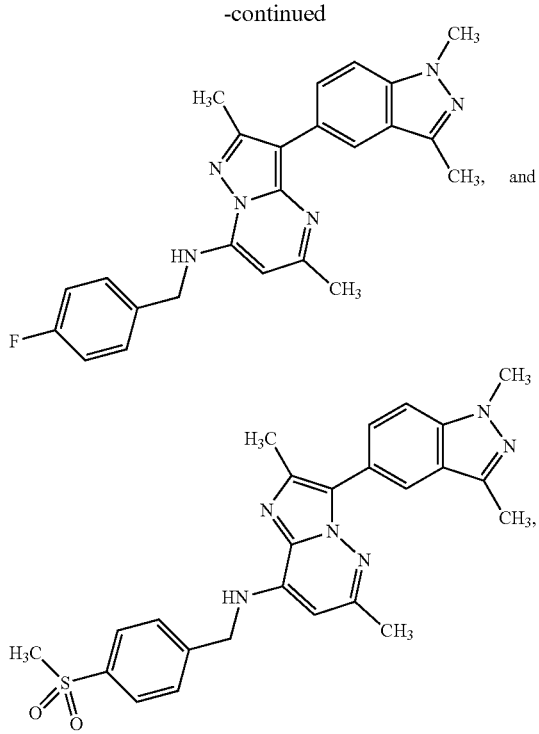

or a pharmaceutically acceptable salt thereof.

12. A pharmaceutical composition comprising a pharmaceutically acceptable excipient and a compound of claim 1, or a pharmaceutically acceptable salt thereof.

13. A method for treating a viral infection in a mammal, comprising administering to the mammal an effective amount of a compound of claim 1, or a pharmaceutically acceptable salt thereof.

14. The method of claim 13, wherein the viral infection is a picornaviral infection.

15. A method for inhibiting phosphatidylinositol kinase activity in a mammal, comprising administering to the mammal an effective amount of a compound of claim 1, or a pharmaceutically acceptable salt thereof.

16. The method of claim 15, wherein the mammal has a disorder or disease linked to abnormal autophagy or impaired autophagy selected from the group consisting of cancer, chronic fatigue syndrome, common cold, conjunctivitis, diabetes, diarrhea, encephalitis, hand-foot-and-mouth disease, herpangina, meningitis, myositis, pancreatitis, paralysis, pleurodynia, poliomyelitis, respiratory illness, sepsis, a cardiac disease, an inflammatory condition, a mucocutaneous lesion, a neuropsychiatric disease, and a neurodegenerative disease.

17. The method of claim 16, wherein the cancer is selected from the group consisting of breast cancer, colorectal cancer, ovarian cancer, and prostate cancer.

18. The method of claim 16, wherein the cardiac disease is myocarditis.

19. The method of claim 16, wherein the neurodegenerative disease is selected from the group consisting of Alzheimer's disease, amyotrophic lateral sclerosis, Huntington's disease, multiple sclerosis, and Parkinson's disease.

* * * * *